US008801746B1

(12) United States Patent
Kreidler et al.

(10) Patent No.: US 8,801,746 B1
(45) Date of Patent: Aug. 12, 2014

(54) SYSTEM AND METHOD FOR DELIVERING A LEFT ATRIAL APPENDAGE CONTAINMENT DEVICE

(75) Inventors: Marc S. Kreidler, Sunnyvale, CA (US); Andrew G. C. Frazier, Sunnyvale, CA (US)

(73) Assignee: Covidien LP, Mansfield, MA (US)

( * ) Notice: Subject to any disclaimer, the term of this patent is extended or adjusted under 35 U.S.C. 154(b) by 1420 days.

(21) Appl. No.: 10/838,710

(22) Filed: May 4, 2004

(51) Int. Cl.
*A61M 29/00* (2006.01)

(52) U.S. Cl.
USPC ....................................................... 606/200

(58) Field of Classification Search
CPC ..... A61F 2/01; A61F 2/013; A61F 2002/016; A61F 2230/0006; A61F 2230/0008; A61F 2230/0071
USPC ................................................. 606/194, 200
See application file for complete search history.

(56) References Cited

U.S. PATENT DOCUMENTS

| 3,402,710 | A | 9/1968 | Paleschuck |
| 3,540,431 | A | 11/1970 | Uddin |
| 3,638,652 | A | 2/1972 | Kelley |
| 3,811,449 | A | 5/1974 | Gravlee et al. |
| 3,844,302 | A | 10/1974 | Klein |
| 3,874,388 | A | 4/1975 | King et al. |
| 4,007,743 | A | 2/1977 | Blake |
| 4,175,545 | A | 11/1979 | Termanini |
| 4,309,776 | A | 1/1982 | Berguer |
| 4,341,218 | A | 7/1982 | Ü |
| 4,603,693 | A | 8/1986 | Conta et al. |
| 4,665,906 | A | 5/1987 | Jervis |
| 4,681,588 | A | 7/1987 | Ketharanathan |
| 4,710,192 | A | 12/1987 | Liotta et al. |
| 4,718,417 | A | 1/1988 | Kittrell et al. |
| 4,759,348 | A | 7/1988 | Cawood |
| 4,827,907 | A | 5/1989 | Tashiro |
| 4,917,089 | A | 4/1990 | Sideris |
| 4,921,484 | A | 5/1990 | Hillstead |
| 4,960,412 | A | 10/1990 | Fink |
| 4,966,150 | A | 10/1990 | Etienne et al. |
| 4,998,972 | A | 3/1991 | Chin et al. |
| 5,041,090 | A | 8/1991 | Scheglov et al. |
| 5,042,707 | A | 8/1991 | Taheri |
| 5,064,435 | A | 11/1991 | Porter |
| 5,071,407 | A | 12/1991 | Termin et al. |

(Continued)

FOREIGN PATENT DOCUMENTS

| WO | WO 96/40356 | 12/1996 |
| WO | WO 98/23322 | 6/1998 |

(Continued)

OTHER PUBLICATIONS

Application and drawings for U.S. Appl. No. 10/642,384, filed Aug. 15, 2003.

*Primary Examiner* — Katherine Dowe
*Assistant Examiner* — Michael Mendoza
(74) *Attorney, Agent, or Firm* — Alana T. Bergman, Esq.

(57) ABSTRACT

A device for containing emboli within a left atrial appendage of a patient includes a frame that is expandable from a reduced cross section to an enlarged cross section and a slider assembly. There is provided in accordance with various embodiments of the present invention methods of preventing retention anchors from projecting outside of the native diameter of the frame, thus facilitating recapture of the device.

37 Claims, 18 Drawing Sheets

(56) References Cited

U.S. PATENT DOCUMENTS

| | | |
|---|---|---|
| 5,078,736 A | 1/1992 | Behl |
| 5,108,418 A | 4/1992 | Lefebvre |
| 5,108,420 A | 4/1992 | Marks |
| 5,108,474 A | 4/1992 | Riedy et al. |
| 5,116,360 A | 5/1992 | Pinchuk et al. |
| 5,122,136 A | 6/1992 | Guglielmi et al. |
| 5,171,259 A | 12/1992 | Inoue |
| 5,176,692 A | 1/1993 | Wilk et al. |
| 5,192,301 A | 3/1993 | Kamiya et al. |
| 5,234,458 A | 8/1993 | Metais |
| 5,258,042 A | 11/1993 | Mehta |
| 5,284,488 A | 2/1994 | Sideris |
| 5,304,184 A | 4/1994 | Hathaway et al. |
| 5,306,234 A | 4/1994 | Johnson |
| 5,312,341 A | 5/1994 | Turi |
| 5,334,217 A | 8/1994 | Das |
| 5,350,399 A | 9/1994 | Erlebacher et al. |
| 5,375,612 A | 12/1994 | Cottenceau et al. |
| 5,397,355 A | 3/1995 | Marin et al. |
| 5,417,699 A | 5/1995 | Klein et al. |
| 5,425,744 A | 6/1995 | Fagan et al. |
| 5,427,119 A | 6/1995 | Swartz et al. |
| 5,433,727 A | 7/1995 | Sideris |
| 5,443,454 A | 8/1995 | Tanabe et al. |
| 5,443,478 A | 8/1995 | Purdy |
| 5,451,235 A | 9/1995 | Lock et al. |
| 5,464,408 A | 11/1995 | Duc |
| 5,490,856 A | 2/1996 | Person et al. |
| 5,497,774 A | 3/1996 | Swartz et al. |
| 5,499,975 A | 3/1996 | Cope et al. |
| 5,522,790 A | 6/1996 | Moll et al. |
| 5,522,836 A | 6/1996 | Palermo |
| 5,527,322 A | 6/1996 | Klein et al. |
| 5,527,338 A | 6/1996 | Purdy |
| 5,558,093 A | 9/1996 | Pomeranz |
| 5,558,652 A | 9/1996 | Henke |
| 5,614,204 A | 3/1997 | Cochrum |
| 5,634,936 A | 6/1997 | Linden et al. |
| 5,643,292 A | 7/1997 | Hart |
| 5,669,933 A | 9/1997 | Simon et al. |
| 5,693,067 A | 12/1997 | Purdy |
| 5,700,285 A | 12/1997 | Myers et al. |
| 5,702,421 A | 12/1997 | Schneidt |
| 5,709,224 A | 1/1998 | Behl et al. |
| 5,709,707 A | 1/1998 | Lock et al. |
| 5,722,400 A | 3/1998 | Ockuly et al. |
| 5,724,975 A | 3/1998 | Negus et al. |
| 5,725,512 A | 3/1998 | Swartz et al. |
| 5,725,552 A | 3/1998 | Kotula et al. |
| 5,725,568 A | 3/1998 | Hastings |
| 5,733,294 A | 3/1998 | Forber et al. |
| 5,735,290 A | 4/1998 | Sterman et al. |
| 5,749,894 A | 5/1998 | Engelson |
| 5,766,219 A | 6/1998 | Horton |
| 5,776,097 A | 7/1998 | Massoud |
| 5,782,860 A | 7/1998 | Epstein et al. |
| 5,800,512 A | 9/1998 | Lentz et al. |
| 5,807,261 A | 9/1998 | Benaron et al. |
| 5,814,028 A | 9/1998 | Swartz et al. |
| 5,814,029 A | 9/1998 | Hassett |
| 5,820,591 A | 10/1998 | Thompson et al. |
| 5,830,228 A | 11/1998 | Knapp et al. |
| 5,833,673 A | 11/1998 | Ockuly et al. |
| 5,836,968 A | 11/1998 | Simon et al. |
| 5,840,027 A | 11/1998 | Swartz et al. |
| 5,843,118 A | 12/1998 | Sepetka et al. |
| 5,848,969 A | 12/1998 | Panescu et al. |
| 5,849,005 A | 12/1998 | Garrison et al. |
| 5,853,422 A | 12/1998 | Huebsch et al. |
| 5,865,791 A | 2/1999 | Whayne et al. |
| 5,879,296 A | 3/1999 | Ockuly et al. |
| 5,879,366 A | 3/1999 | Shaw et al. |
| 5,891,558 A | 4/1999 | Bell et al. |
| 5,904,680 A | 5/1999 | Kordis et al. |
| 5,906,207 A | 5/1999 | Shen |
| 5,935,148 A | 8/1999 | Villar et al. |
| 5,961,545 A | 10/1999 | Lentz et al. |
| 6,004,280 A | 12/1999 | Buck et al. |
| 6,004,348 A | 12/1999 | Banas et al. |
| 6,007,557 A | 12/1999 | Ambrisco et al. |
| 6,066,126 A | 5/2000 | Li et al. |
| 6,076,012 A | 6/2000 | Swanson et al. |
| 6,079,414 A | 6/2000 | Roth |
| 6,080,182 A | 6/2000 | Shaw et al. |
| 6,090,084 A | 7/2000 | Hassett et al. |
| 6,096,053 A | 8/2000 | Bates |
| 6,124,523 A | 9/2000 | Banas et al. |
| 6,132,438 A | 10/2000 | Fleischman et al. |
| 6,139,573 A | 10/2000 | Sogard et al. |
| 6,152,144 A | 11/2000 | Lesh et al. |
| 6,171,329 B1 | 1/2001 | Shaw et al. |
| 6,203,531 B1 | 3/2001 | Ockuly et al. |
| 6,231,589 B1 | 5/2001 | Wessman et al. |
| 6,245,012 B1 | 6/2001 | Kleshinski |
| 6,285,898 B1 | 9/2001 | Ben-Haim |
| 6,290,674 B1 | 9/2001 | Roue et al. |
| 6,368,338 B1 | 4/2002 | Kónya et al. |
| 6,371,971 B1 | 4/2002 | Tsugita et al. |
| 6,391,044 B1 | 5/2002 | Yadav et al. |
| 6,402,746 B1 | 6/2002 | Whayne et al. |
| 6,443,972 B1 | 9/2002 | Bosma et al. |
| 6,468,291 B2 | 10/2002 | Bates et al. |
| 6,488,689 B1 | 12/2002 | Kaplan et al. |
| 6,517,573 B1 | 2/2003 | Pollock et al. |
| 6,551,303 B1 | 4/2003 | Van Tassel et al. |
| 6,558,405 B1 | 5/2003 | McInnes |
| 6,562,058 B2 | 5/2003 | Seguin et al. |
| 6,652,555 B1 | 11/2003 | Van Tassel et al. |
| 6,652,556 B1 | 11/2003 | Van Tassel et al. |
| 6,689,150 B1 | 2/2004 | Van Tassel et al. |
| 6,994,092 B2 * | 2/2006 | van der Burg et al. ........ 128/887 |
| 2001/0034537 A1 | 10/2001 | Shaw et al. |
| 2002/0022860 A1 | 2/2002 | Borillo et al. |
| 2002/0035374 A1 | 3/2002 | Borillo et al. |
| 2002/0062133 A1 | 5/2002 | Gilson et al. |
| 2002/0111647 A1 | 8/2002 | Khairkhahan et al. |
| 2002/0138094 A1 | 9/2002 | Borillo et al. |
| 2002/0138097 A1 | 9/2002 | Ostrovsky et al. |
| 2002/0177855 A1 | 11/2002 | Greene, Jr. et al. |
| 2003/0125797 A1 * | 7/2003 | Chobotov et al. ............ 623/1.13 |
| 2003/0181942 A1 | 9/2003 | Sutton et al. |
| 2003/0191526 A1 | 10/2003 | Van Tassel et al. |
| 2004/0087999 A1 * | 5/2004 | Bosma et al. ................. 606/200 |

FOREIGN PATENT DOCUMENTS

| | | |
|---|---|---|
| WO | WO 98/27868 | 7/1998 |
| WO | WO 99/23976 | 5/1999 |
| WO | WO 99/25252 | 5/1999 |
| WO | WO 99/44510 | 10/1999 |
| WO | WO 00/16705 | 3/2000 |
| WO | WO 00/27292 | 5/2000 |
| WO | WO/02/24106 A2 | 3/2002 |
| WO | WO 02/071977 | 9/2002 |

* cited by examiner

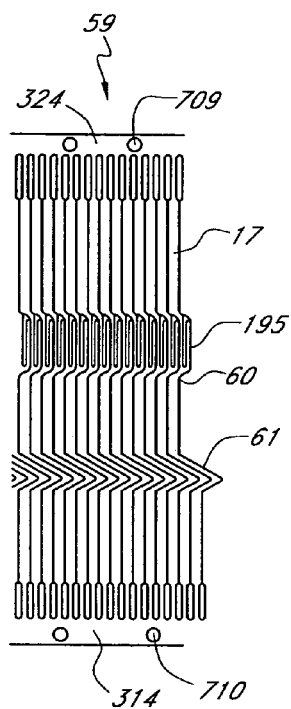
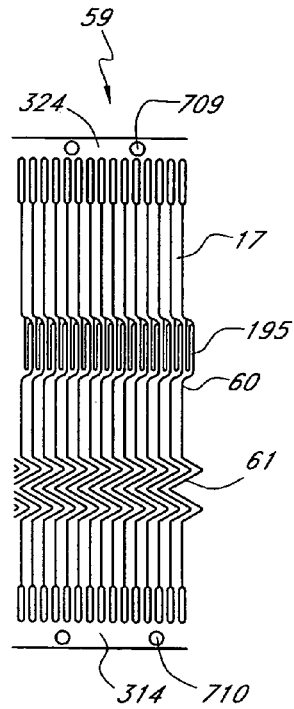
FIG. 2A  FIG. 2B
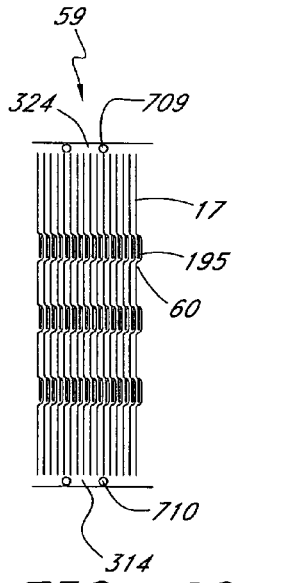
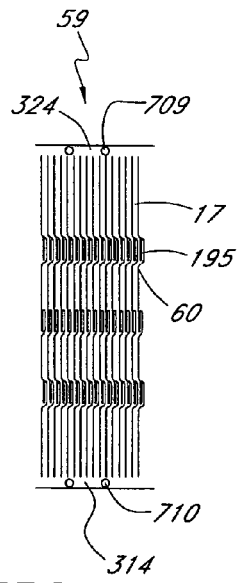
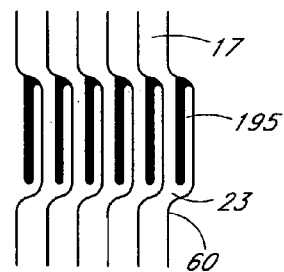
FIG. 2C  FIG. 2D  FIG. 2E
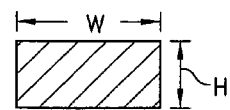
FIG. 2F

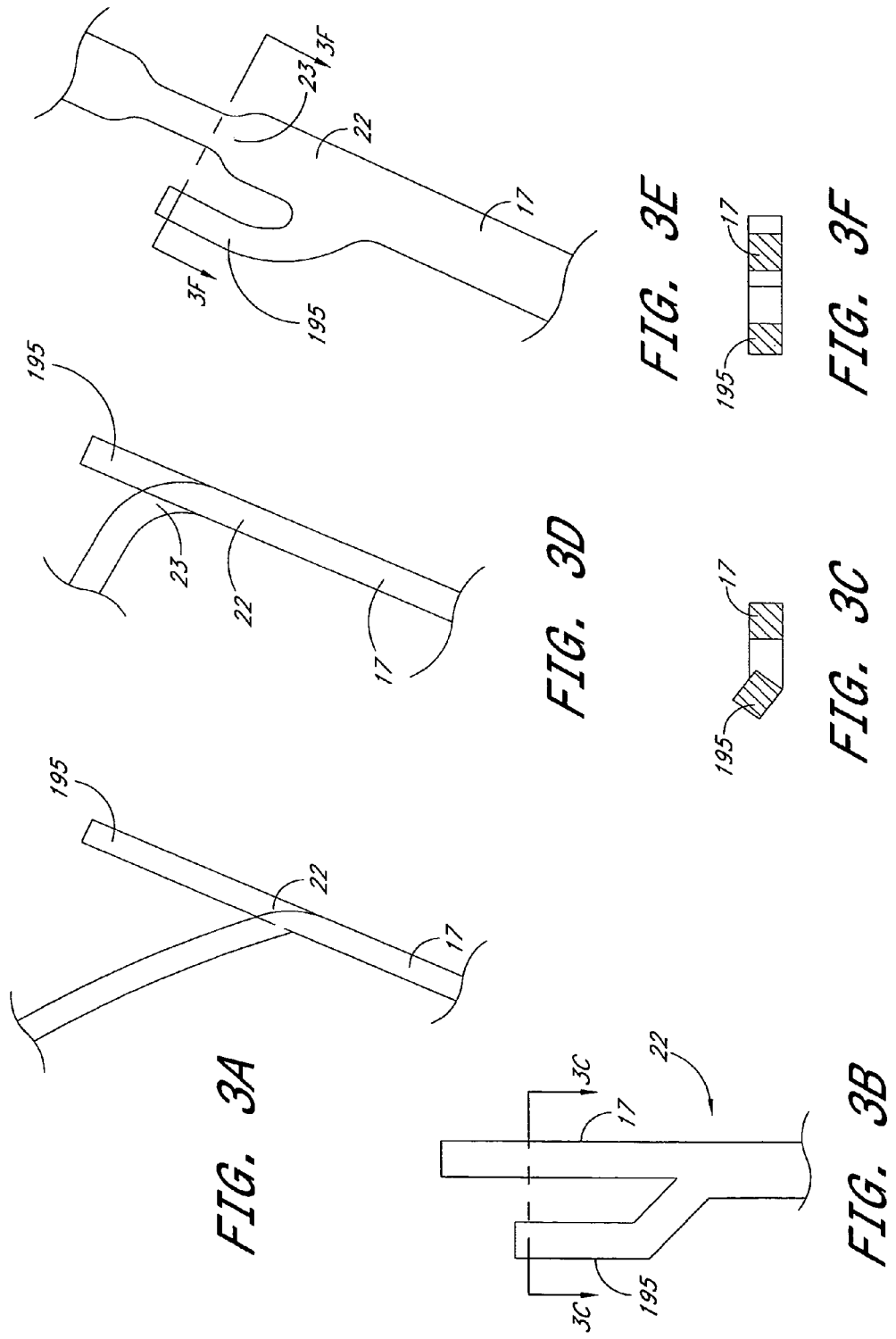

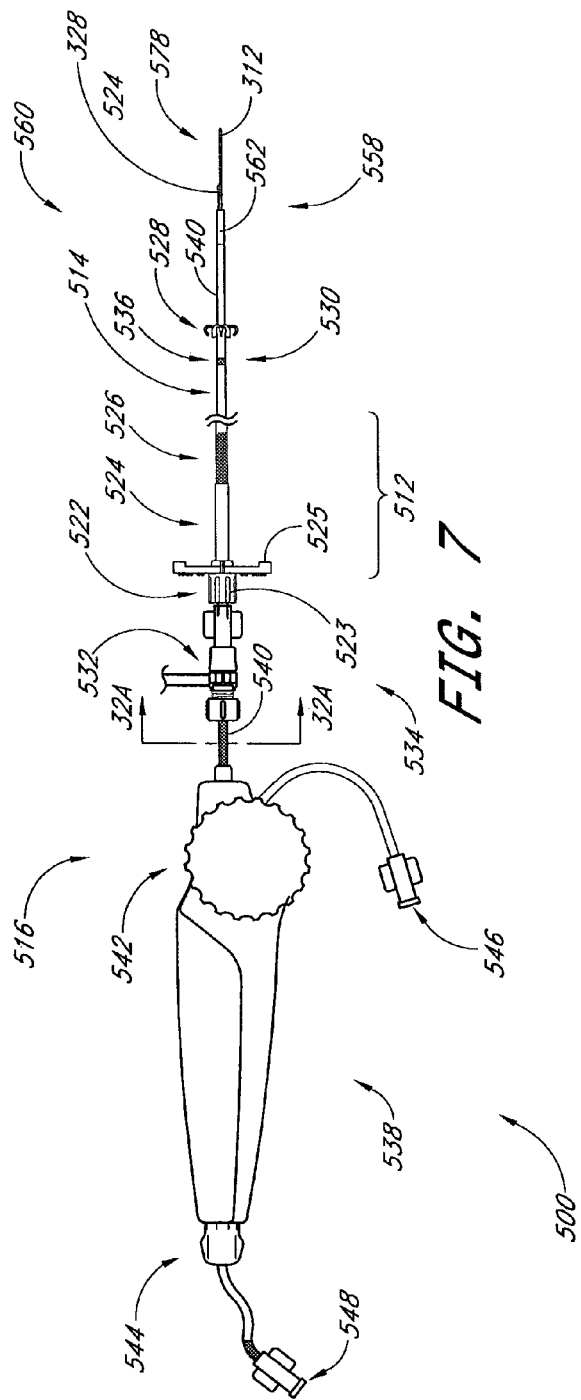
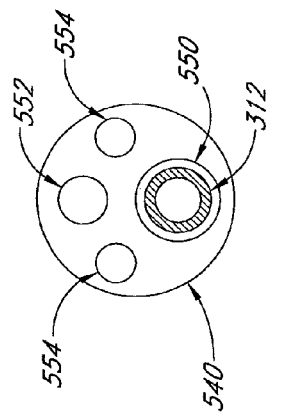

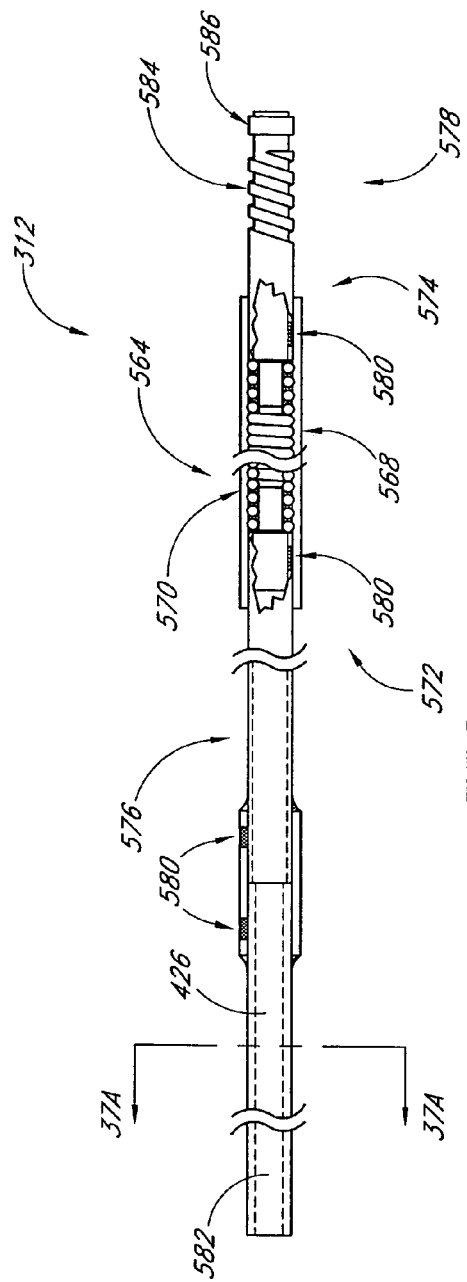
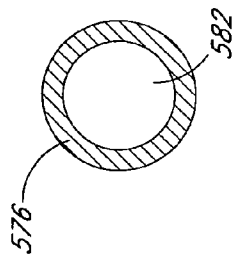
FIG. 12
FIG. 12A

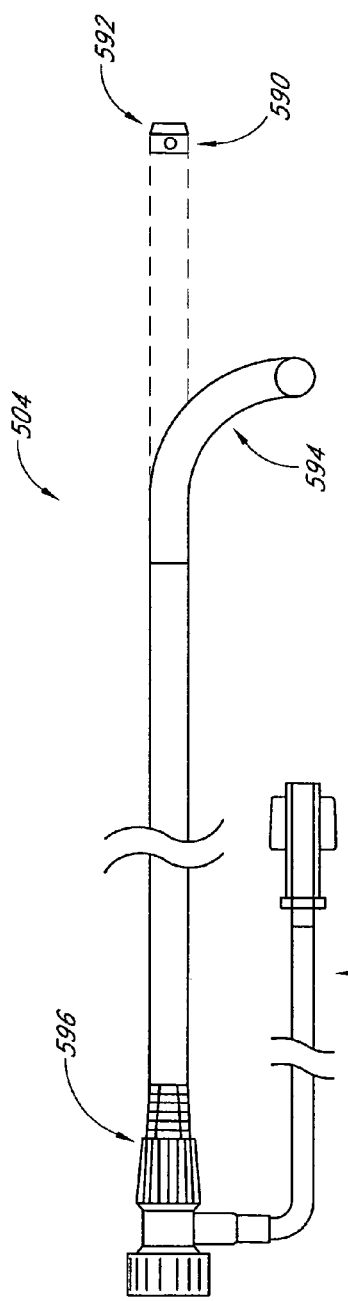
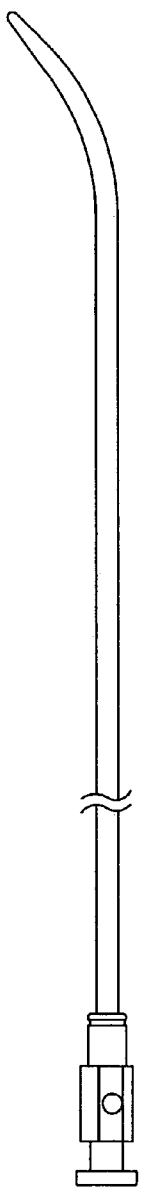
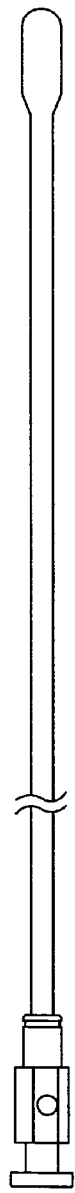
FIG. 13A
FIG. 13B
FIG. 13C

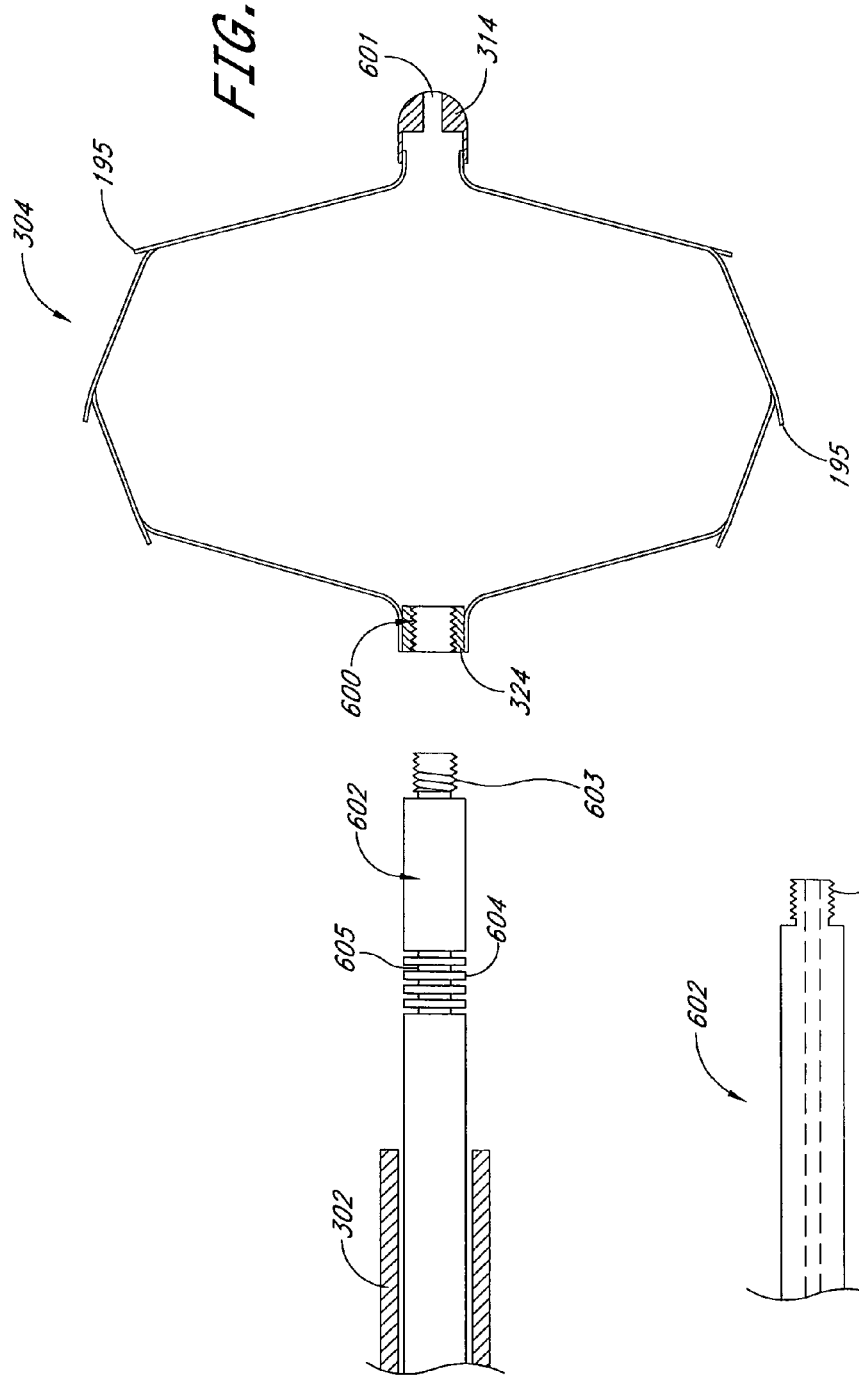
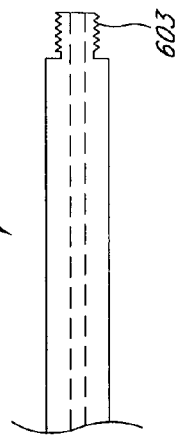

SYSTEM AND METHOD FOR DELIVERING A LEFT ATRIAL APPENDAGE CONTAINMENT DEVICE

BACKGROUND OF THE INVENTION

Embolic stroke is the nation's third leading killer for adults, and is a major cause of disability. There are over 700,000 strokes per year in the United States alone. Of these, roughly 100,000 are hemorrhagic, and 600,000 are ischemic (either due to vessel narrowing or to embolism). The most common cause of embolic stroke emanating from the heart is thrombus formation due to atrial fibrillation. Approximately 80,000 strokes per year are attributable to atrial fibrillation. Atrial fibrillation is an arrhythmia of the heart that results in a rapid and chaotic heartbeat that produces lower cardiac output and irregular and turbulent blood flow in the vascular system. There are over five million people worldwide with atrial fibrillation, with about four hundred thousand new cases reported each year. Atrial fibrillation is associated with a 500 percent greater risk of stroke due to the condition. A patient with atrial fibrillation typically has a significantly decreased quality of life due, in part, to the fear of a stroke, and the pharmaceutical regimen necessary to reduce that risk.

For patients who develop atrial thrombus from atrial fibrillation, the clot normally occurs in the left atrial appendage (LAA) of the heart. The LAA is a cavity which looks like a small finger or windsock and which is connected to the lateral wall of the left atrium between the mitral valve and the root of the left pulmonary vein. The LAA normally contracts with the rest of the left atrium during a normal heart cycle, thus keeping blood from becoming stagnant therein, but often fails to contract with any vigor in patients experiencing atrial fibrillation due to the discoordinate electrical signals associated with AF. As a result, thrombus formation is predisposed to form in the stagnant blood within the LAA. The containment of thrombus formed within the LAA of patients with atrial fibrillation could significantly reduce the incidence of stroke in those patients.

Blackshear and Odell have reported that of the 1288 patients with non-rheumatic atrial fibrillation involved in their study, 221 (17%) had thrombus detected in the left atrium of the heart. Blackshear J L, Odell J A., Appendage Obliteration to Reduce Stroke in Cardiac Surgical Patients With Atrial Fibrillation. *Ann Thorac. Surg.*, 1996.61 (2):755-9. Of the patients with atrial thrombus, 201 (91%) had the atrial thrombus located within the left atrial appendage. The foregoing suggests that the elimination or containment of thrombus formed within the LAA of patients with atrial fibrillation would significantly reduce the incidence of stroke in those patients.

Pharmacological therapies for stroke prevention such as oral or systemic administration of warfarin or the like have been inadequate due to serious side effects of the medications and lack of patient compliance in taking the medication. Invasive surgical or thoroscopic techniques have been used to obliterate the LAA, however, many patients are not suitable candidates for such surgical procedures due to a compromised condition or having previously undergone cardiac surgery. In addition, the perceived risks of even a thoroscopic surgical procedure often outweigh the potential benefits. See Blackshear and Odell, above. See also Lindsay B D., Obliteration of the Left Atrial Appendage: A Concept Worth Testing, Ann Thorac. Surg., 1996.61 (2):515.

SUMMARY OF THE INVENTION

One preferred embodiment of the present invention is a device for containing emboli within a left atrial appendage of a patient. The device comprises an implantable frame that is expandable from a reduced cross section to an enlarged cross section, and having a barrier provided thereon. The frame comprises metallic struts or supports that are advanceable from a generally axially extending orientation such as to fit within a tubular introduction catheter to a radially inclined orientation following deployment from the catheter. In a self-expandable embodiment, the struts are biased radially outwardly such that the device expands to an enlarged, implantation cross-section under its own bias following deployment from the catheter.

The device is preferably provided with one or more retention structures for retaining the device in the left atrial appendage or other body cavity or lumen. A plurality of barbs or other anchors are provided, for engaging adjacent tissue to retain the device in its implanted position and to limit relative movement between the tissue and the device. The anchors are preferably provided on one or more of the struts, or other portion of frame. Preferably, every strut, every second strut, or every third strut are provided with one or two or more anchors each.

Existing methods of employing anchors, barbs, or hooks as retention structures for retaining the device in the left atrial appendage or other body cavity or lumen can be problematic due to the natural tendency of an individual anchor to bend and assume an outward configuration, even when the frame is collapsed. This causes the anchors to loft outside the diameter that they normally would assume if they remained in the planar axis of the collapsed frame. One undesirable and problematic consequence of this bending of the anchors is difficulty in recapturing the frame should an operator desire to retrieve the device, for example, through a retrieval catheter. Similar, previous designs of anchors and struts which do allow more effective recapture of the device do not allow for sufficient pronation of the anchors when the device is in an expanded state.

There is provided in accordance with one embodiment of the present invention a selective arrangement of tissue anchors along a radially deformed, curved or inclined cross section of an expandable device, such as a left atrial appendage containment device, to allow preferential pronation of the anchors either into or out of the plane of engagement.

One preferred embodiment comprises manipulating the aspect ratio of a deformable strut or support of the expandable device in order to allow for more or less outward bending and/or tipping of an attached tissue anchor. Aspect ratio is defined as the width divided by height of the native strut in the middle of its bending section, where height in this case is equal to the wall thickness of the implant frame. The amount and direction of bending of the struts may be dependent upon the aspect ratio of the section and on the geometry of the attached anchor. The implant is preferably designed to balance the amount of anchoring appropriate for the application and recapturability.

Additional preferred embodiments of the struts or spokes comprise cutting patterns which result in jogged segments, wherein the spoke or strut curves away from the longitudinal axis of the struts or spokes, e.g., to the inside and/or outside. Preferred embodiments may further comprise turbo elements, which are exaggerated forms of jogged segments. Preferred embodiments may contain a plurality of jogs and/or turbo elements on a given strut or spoke. Struts or spokes may preferably comprise various combinations of jogged segments, segments with altered aspect ratios, and segments with turbo elements.

Preferred embodiments of the approach to control the position of anchors on an implantable device further comprise several possible combinations of strut and anchor alterations. One specific embodiment comprises moving the bend point of the strut with respect to the anchor and making the bend more gradual. Additionally, the anchors can be preferably located on the same side toward which the jogged segment turns.

Another preferred embodiment of the current invention comprises an additional bend placed distal to a tissue anchor, which forces the tissue anchor downward upon collapse of the implant. In one preferred embodiment, the additional distal bend for recapture removes the necessity for a recapture sheath.

The approaches of manipulating the aspect ratio of a deformable strut and utilizing distal bends render implantable devices having tissue anchors easier to recapture, safer if inadvertently recaptured, and lower in cost.

Preferred embodiments of the implantable device comprise an expandable frame that is moveable between a collapsed configuration and an expanded configuration. The expandable frame has a proximal end and a distal end and a plurality of supports each having a length that extends at least partially between the proximal end and the distal end, the length defining a longitudinal axis of each support when the frame is in the collapsed configuration. A plurality of tissue anchors is attached to corresponding supports. In preferred embodiments, the frame is self-expanding. Preferred embodiments of the frame comprise a proximal hub and a distal hub, and the supports form struts extending between the proximal and distal hubs. A barrier is preferably attached to a portion of the expandable frame. In preferred embodiments, the frame is sized and configured for placement within a left atrial appendage of a patient.

In preferred embodiments of the present invention, a plurality of anchors are attached to each support. Particularly preferred embodiments comprise a proximal, intermediate and distal anchor attached to each support. In accordance with preferred embodiments, the anchors are integrally formed with the supports. The supports and anchors are preferably metallic, and in preferred embodiments the supports and anchors may be cut from a tube.

The anchors of the implantable device are preferably attached adjacent to a jogged portion along the length of a corresponding support. In accordance with preferred embodiments, the jogged portion turns at least partially away from the longitudinal axis of the support when the frame is in the collapsed configuration.

In preferred embodiments, the anchors have a tissue engagement end extending generally toward the proximal end of the expandable frame when the frame is in the collapsed configuration. In accordance with embodiments of the present invention, the anchors are attached proximal to a jogged portion along the length of a corresponding support. In preferred embodiments the anchors are attached alongside a side of the support toward which said jogged portion turns. In preferred embodiments of the device the jogged portion turns away from the support longitudinal axis by about 15 degrees or more. In alternative preferred embodiments the jogged portion turns away from the support longitudinal axis by about 30 degrees or more.

One embodiment of the implantable device comprises an expandable frame that is moveable between a collapsed configuration and an expanded configuration. The expandable frame has a proximal end and a distal end. A plurality of supports each has a length that extends at least partially between the proximal end and the distal end. A plurality of tissue anchors is attached to corresponding supports and extends at least partially alongside a portion of said corresponding supports. In particularly preferred embodiments, the supports have an aspect ratio that decreases in said portion alongside said anchors to form a bending region of said supports. In embodiments of the implantable device, the bending region preferably has an aspect ratio in the range of about 1:1 to about 2:1. In alternative embodiments, the bending region has an aspect ratio in the range of about 1.5:1 or about 1.25:1.

In preferred embodiments, the anchors are attached adjacent to a jogged portion along the length of a corresponding support. Particularly preferred embodiments comprise a plurality of anchors which are attached to each support, each preferably being attached adjacent a bending region of said supports having a decreased aspect ratio alongside said anchors. The bending region has a decreased aspect ratio that may be preferably spaced from an attachment location between the anchor and the corresponding support.

Further preferred embodiments of the implantable device comprise supports having an aspect ratio that decreases in a portion alongside the anchors to form a bending region of said supports, and said anchors are attached proximal to a jogged portion along the length of a corresponding support distal, wherein the jogged portion preferably turns at least partially away from the longitudinal axis of the support when the frame is in the collapsed configuration.

An alternative preferred embodiment comprises supports having at least a first bending region adjacent an anchor and a second bending region spaced distally from said anchor, said second bending region having an aspect ratio greater than that of the first bending region.

BRIEF DESCRIPTION OF THE DRAWINGS

FIGS. 2A-2D show a schematic view of cutting formations of multiple struts along the length of a metal tube;

FIG. 2E shows a close up view of a strut with a jogged segment distal to an anchor;

FIG. 2F is a cross-sectional view of a portion of a strut, showing aspect ratio measurements.

FIGS. 3A-3C show the bending of a strut at the anchor-strut junction of a containment device;

FIG. 3D shows a preferred bend of a strut away from the anchor-strut junction;

FIG. 3E shows another view of a preferred bend of a strut away from the anchor-strut junction;

FIG. 3F shows a cross-sectional view of an anchor and strut of FIGS. 3E and 3D.

FIG. 7 is a schematic view of a delivery system constructed in accordance with one embodiment of the present invention;

FIG. 7A is a cross sectional view of a deployment catheter as shown in FIG. 9, taken along cut line 7A-7A.

FIG. 12 is a partial cross sectional view of an axially moveable core used in the system of FIG. 7;

FIG. 12A is a cross sectional view of the axially moveable core of FIG. 12 taken along cut line 12A-12A; and FIGS. 13A-13C are a schematic view of a transseptal sheath used in combination with the system of FIG. 7.

FIG. 14 is a schematic view of a delivery system constructed in accordance with one embodiment of the present invention;

FIG. 15 is a close up view of the delivery wire of the system of FIG. 14;

DETAILED DESCRIPTION OF THE PREFERRED EMBODIMENTS

Figure 1:
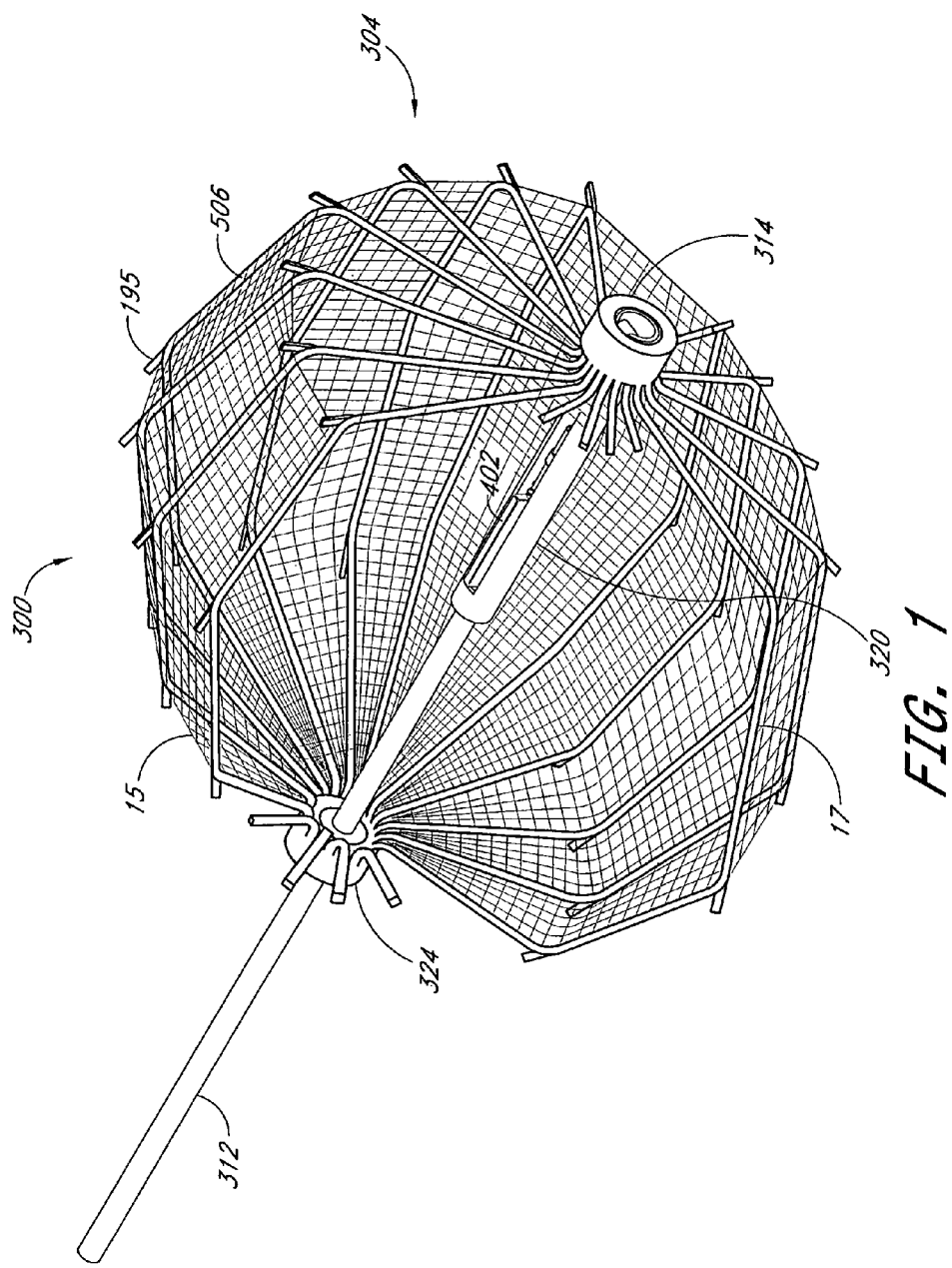
FIG. 1 is a perspective view of a containment device in accordance with one embodiment of the present invention.

Referring to FIG. 1, there is illustrated an implantable device 304 in accordance with one embodiment of the present invention. Although the present invention will be described primarily in the context of an implantable device with a barrier for containing particles within a left atrial appendage of a patient, the present inventors also contemplate r that other devices may utilize features of the preferred embodiments as described herein. For example, embodiments described herein may be used, without limitation, for: closure of atrial septal defects; closure of a patent foramen ovale in patients with recurrent cryptogenic stroke due to presumed paradoxical embolism; closure of patent ductus arteriosus; and to occlude muscular ventricular septal defects. The preferred embodiments may also have applicability to other devices that may utilize anchors.

The implantable device 304 comprises an expandable frame 506. In the illustrated embodiment, the frame 506 comprises a plurality of radially outwardly extending supports, struts or spokes 17 each having a collapsed length within the range of from about 0.5 cm to about 5 cm from a proximal hub 324 to a distal hub 314. In one embodiment, the struts 17 have an axial length of about 1.5 cm. It will be appreciated that although struts are described as extending between proximal and distal hubs, any implantable device having supports that extend at least partially between a proximal and distal end of the device may incorporate features of the preferred embodiments described herein. Depending upon the desired introduction crossing profile of the collapsed device 304, as well as structural strength requirements in the deployed device 304, anywhere within the range of from about 3 struts to about 40 struts may be utilized. In some embodiments, anywhere from about 12 to about 24 struts are utilized, and, 18 struts are utilized in one embodiment.

The struts 17 are advanceable from a generally axially extending orientation such as to fit within a tubular introduction catheter (not shown) to a radially inclined orientation as illustrated in FIG. 1 following deployment from the catheter. In a self-expandable embodiment, the struts 17 are biased radially outwardly such that the device 304 expands to its enlarged, implantation cross-section under its own bias following deployment from the catheter. Alternatively, the device 304 may be enlarged using any of a variety of enlargement structures such as an inflatable balloon, or a catheter for axially shortening the occlusion member. In the illustrated embodiment, each of the struts 17 extends between a proximal hub 324 and a distal hub 314. The proximal and distal hubs may be cylindrical tubular sections, and in one embodiment, the struts 17 are formed from a longitudinally cut tube integral with the hubs 324 and 314. In one embodiment, the struts are formed from a shape memory material such as nickel titanium. As illustrated, the struts 17, when in their expanded configuration, have segments that extend outward and are inclined relative to a longitudinal axis of the device.

As shown in FIG. 1, a barrier 15 is provided over at least a proximal face of the device 304. The barrier 15 may comprise any of a variety of materials which facilitate cellular ingrowth, such as ePTFE. The suitability of alternate materials for barrier 15 can be determined through routine experimentation by those of skill in the art. The barrier 15 may be provided on either one or both sides of the struts 17. In one embodiment, the barrier 15 comprises two layers, with one layer on each side of the frame 506. The two layers may be bonded to each other around the struts 17 in any of a variety of ways, such as by heat bonding with or without an intermediate bonding layer such as polyethylene or FEP, adhesives, sutures, and other techniques which will be apparent to those of skill in the art in view of the disclosure herein. The barrier 15 preferably has a thickness of no more than about 0.003" and a porosity within the range of from about 5 μm to about 60 μm.

In one preferred embodiment, the struts comprise a metal such as stainless steel, nitinol, Elgiloy, or others which can be determined through routine experimentation by those of skill in the art. Wires having a circular or rectangular cross-section may be utilized depending upon the manufacturing technique. In one embodiment, rectangular cross section struts are cut such as by known laser cutting techniques from tube stock, a portion of which forms the hubs 324 and 314.

As illustrated in FIG. 1, the device 304 is preferably provided with one or more retention structures for retaining the device in the left atrial appendage or other body cavity or lumen. In the illustrated embodiment, a plurality of barbs or other anchors 195 are provided, for engaging adjacent tissue to retain the device in its implanted position and to limit relative movement between the tissue and the device. Each anchor can be laser cut from the corresponding strut 17. The anchors are attached directly to a section of strut 17 that is adjacent to a bend section upon expansion; the different bias of the strut sections causes them to project out. The illustrated anchors are provided on one or more of the struts 17, or other portion of frame 506. Preferably, every strut, every second strut, or every third strut are provided with one or two or more anchors each.

The illustrated anchor 195 is in the form of a barb, with one or more on each strut for extending into tissue for example, at or near the opening of the LAA. Depending upon the embodiment, two or three barbs may alternatively be desired on each strut. In the embodiment of FIG. 1, each of three barbs on a strut is inclined in a generally proximal direction. This is to inhibit proximal migration of the implant out of the left atrial appendage; or other opening. In this context, distal refers to the direction into the left atrial appendage, and proximal refers to the direction from the left atrial appendage into the left atrium of the heart.

Alternatively, one or more barbs may face distally, to inhibit distal migration of the device 304 deeper into the LAA. In one preferred embodiment, a proximal plurality of barbs may be inclined in a first direction, and a distal plurality of barbs may be inclined in a second direction, to anchor the implant against both proximal and distal migration.

Any of a wide variety of structures may be utilized for anchor 195 on the device 304 such as hooks, barbs, pins, sutures, adhesives, ingrowth surfaces and others which will be apparent to those of skill in the art in view of the disclosure herein.

In use, the device 304 is preferably positioned within a tubular anatomical structure to be contained or occluded such as the left atrial appendage. In a left atrial appendage application, the device 304 is positioned across or near the opening to the LAA. Further details regarding use of the device are described below. Additional detail on device structures that may be used in combination with preferred embodiments as described herein are contained in Applicant's copending application Ser. No. 10/033,371, filed Oct. 19, 2001 and published on Aug. 15, 2003 as U.S. Publication No. 2002-0111647, Ser. No. 10/642,384, filed Aug. 15, 2003, and U.S. Pat. No. 6,152,144, the entire contents of each of which are hereby incorporated by reference.

FIGS. 2A-2E represent different cutting formations of multiple struts 17 and anchors 195 along the length of a metal tube 59, schematically shown extending between proximal hub 324 and distal hub 314. FIG. 2E shows a close up view of a portion of the struts 17 of FIG. 2C, and more particularly shows an anchor 195 extending alongside a portion of the strut with a tissue engaging end extending generally toward the proximal hub. For reference, the anchors 195 are described herein as being positioned on the outer side of the corresponding strut. Each strut 17 can be considered to define an overall longitudinal axis, and each strut includes a jogged portion 60 located distal to the anchors. In the jogged portion 60, the strut curves toward the outer side of the strut 17, turning away from the longitudinal axis of the strut (extending distal to proximal) before reaching the attachment location of the anchor 195. At or after each anchor, the strut curves back toward the inner side of the strut 17.

In the preferred embodiments of FIGS. 2A-2E, the anchors 195 are located on the outer side of the struts 17. In particularly preferred embodiments, the anchor is located on the same side of the strut 17 toward which the jog 60 is directed. The jog 60 allows twisting to occur during expansion and retraction of the device, thus helping the anchor to project radially outward when the frame is expanded. Conversely, the jog 60 allows the anchor to twist back into the struts' planar axis when the frame is retracted. In preferred embodiments, the jogs comprise about a fifteen degree movement or more, away from the neutral longitudinal axis and toward the outer side, of the strut 17. In alternate embodiments, the jogs 60 comprise about a thirty degree movement or more, away from the neutral axis and toward the outer side, of the strut 17. In additional embodiments, the jogs 60 comprise about a forty-five degree movement or more, away from the neutral axis and toward the outer side, of the strut 17. Preferred embodiments of jogs 60 may also comprise about a sixty degree movement or more, away from the neutral axis and toward the outer side, of the strut 17. In the preferred embodiment of FIG. 2C, the portions of the struts 17 proximal to the anchors 195 curve back toward the inner side to return to the same longitudinal axis as that portion of the struts 17 distal to the jog 60. In the preferred embodiment of FIG. 2D, the portions of the struts 17 proximal to the middle anchors 195 do not curve back toward the inner side to return to the same longitudinal axis as that portion of the struts 17 distal to the jog 60.

The preferred embodiments shown in FIGS. 2A and 2B additionally comprise turbo elements 61 distal to the jog 60 and anchors 195, which in FIG. 2A are "V"-shaped and in FIG. 2B are "W"-shaped. The turbo elements 61 are cutting formations that deviate from the neutral longitudinal axis of the struts 17 in order to facilitate twisting of anchors into and out of the planar axis. The turbo elements 61 function similarly to the jogs 60 by allowing preferential twisting of the struts 17 during bending of the frame. The turbo elements 61 are preferably located further away from the anchors 195 than the jogs 60, and may have a more pronounced deviation from the longitudinal axis than the jogged region. As indicated in FIG. 2A, preferred embodiments may comprise turbo elements 61 which curve to the outside, then to the inside. Alternatively, as shown in FIG. 2B, the turbo elements 61 may preferably curve to the outside, then inside, then outside, then back to the inside. These turbo elements may deviate from the overall longitudinal axis of the struts by the same angles mentioned for the jog sections above. Other embodiments preferably comprise various other combinations of curves which form the turbo elements. Preferred embodiments of the device may comprise a plurality of turbo elements and/or jogged regions.

As shown in FIG. 2E, a bending region 23 of the strut 17 is located adjacent to the anchors 195, preferably proximal to the jog 60. In this region, the aspect ratio of the strut reduces to promote bending of the strut. FIG. 2F illustrates a cross-section of the strut 17 having a width W and a height H. Preferred embodiments of the device comprise struts with aspect ratios of width to height, at the bending regions 23 of the struts, in the range of about 1:1 to 2:1. One preferred embodiment of the device has an aspect ratio in the bending region of about 1.5:1, about 1.25:1 or 1:1. These reduced aspect ratios may also be found in the turbo elements 61. Proximal and distal to the bending regions 23 or turbo elements 61, and even in the jogged portion 60, the strut 17 may have a constant aspect ratio, larger than the aspect ratio of the bending region, which in one embodiment, is about 2:1. In one embodiment, the aspect ratio in the jogged portion 60 may be intermediate between the aspect ratio of the bending region 23 and the aspect ratio of the strut proximal to the anchor and distal to the jogged portion, and in one embodiment, where the bending region 23 has an aspect ratio of about 1:1, the jogged portion has an aspect ratio of about 1.25:1. In particularly preferred embodiments of the device, the aspect ratio of the struts immediately adjacent to the proximal and distal hubs may also be reduced, and in one embodiment, has a ratio of about 1:1, in order to facilitate bending adjacent the hubs.

Additional preferred embodiments comprise varying the aspect ratios at different sections of the struts. Altering the aspect ratio of the jogged or turbo sections can enhance or minimize the twisting effect.

FIG. 2E further illustrates that in the bending region 23, proximal to the jogged portion 60, the strut continues to extend for a length parallel to the longitudinal axis of the strut 17 but defining its own axis spaced away from longitudinal axis of the overall strut. The anchors 195 in this embodiment are thus spaced outside the overall longitudinal axis defined by the struts 17. Alternatively, as shown in FIGS. 2A and 2B, the longitudinal axis of this length along the bending region 23 coincides with the longitudinal axis of the overall strut, with the anchors located within the overall longitudinal axis of the struts. As shown in FIG. 2E, the anchor 195 may extend over substantially the entire length of the bending region 23, or may be shorter than the bending region. In preferred embodiments, the length of the anchors is about 0.5-10 mm, more preferably about 1-5 mm, and even more preferably about 2-3 mm. In preferred embodiments, the length of the bending region is about 1-15 mm, more preferably about 2-7 mm, and even more preferably about 3-5 mm.

In another embodiment, the bending location of a strut can be modified to produced desired anchor lofting. Referring to FIGS. 3A-3C, there is illustrated a strut 17 of a frame 506 that may create undesired lofting of an attached anchor 195. As shown in FIG. 3A, it is observed that some struts may be shape set to bend at a junction 22 between a strut itself 17 and its tissue anchor 195. In the anchor-junction configuration in FIG. 3A, straightening of the strut 17 during collapsing of the frame for recapture may allow the anchor 195 to continue to project radially-outwardly, remaining outside of the native diameter of the collapsed frame. As illustrated in FIG. 3C, which represents a cross-sectional view of the strut 17 and anchor 195 taken through line 3C-3C of FIG. 3B, when the strut 17 is bent along its axis, bending of the strut over a short distance can cause kinks that twist the strut and causes the strut to form a trapezoidal transverse cross-section. This can have the effect of lofting the attached tissue anchor farther outside the diameter of the frame than it normally would be if it remained in the planar axis.

In one embodiment of the invention, as shown in FIGS. 3D-3F, the strut 17, which preferably has a rectangular cross-sectional dimension shown in FIG. 3F, has a bending region 23 which is relocated away from the strut-anchor junction 22, either proximally or distally away from the junction 22, to reduce or prevent the undesired projection of the anchor 195 outside of the native diameter. As illustrated in FIG. 3E, the bending region 23 is moved proximally away from the junction 22, preferably about half the distance of the length of the adjoining anchor 195. In one embodiment, where the anchor has a length of about 3 mm, the bending region begins about 2 mm proximal to the junction 22. In one embodiment, the bending region 23 extends over a length of about 2 mm, and extends past the tissue engaging end of the anchor 195. Moreover, relocation and lengthening of the bend 23 allows strut bending to occur over a greater distance, which reduces the occurrence of kinks. In one embodiment, the bending region 23 has an aspect ratio of about 1:1, compared to an aspect ratio proximal and distal to the bending region of about 2:1.

In another embodiment, illustrated in FIGS. 4A-4F, struts 17 include a bend section 66 positioned distal to tissue anchor 195, that forces the tissue anchor downward upon collapse of the implant. This embodiment renders devices easier to recapture, safer if inadvertently recaptured, and lower in cost (for example, by removing the need for a recapture sheath), while providing the equivalent performance as existing approaches.

Figure 4A:
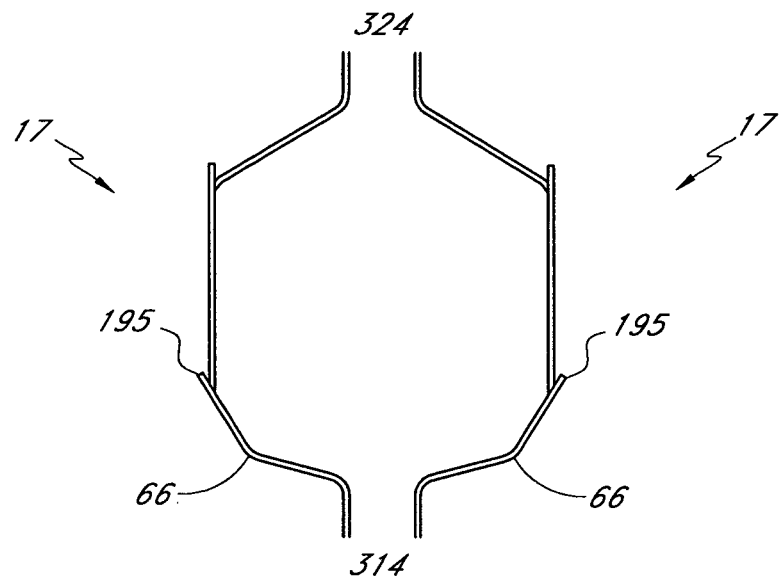
FIG. 4A is partial cross-sectional view of an expandable frame, showing the position of a distal bend with reference to a distal anchor.
Figure 4E:
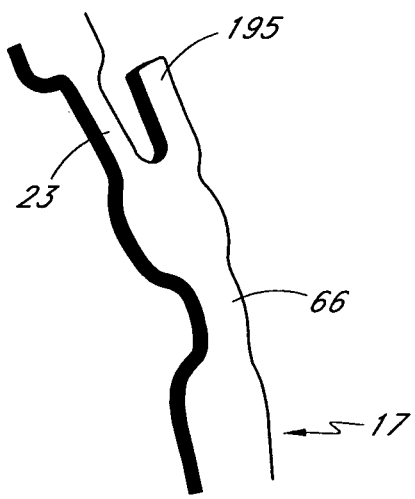
FIG. 4E is a perspective close up view of the strut of FIG. 4B, showing the distal bend in relation to the anchor.
Figure 4B:
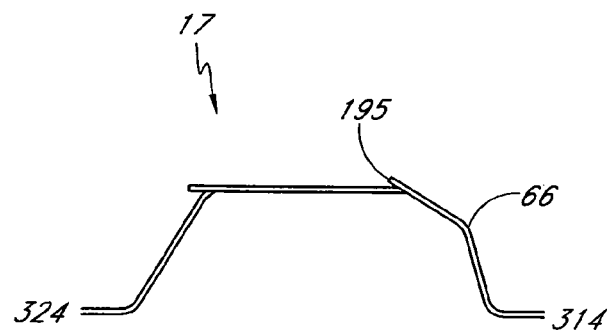
FIG. 4B is a schematic side view of the strut in an expanded configuration, showing the position of a distal bend with reference to the distal anchor.
Figure 4C:
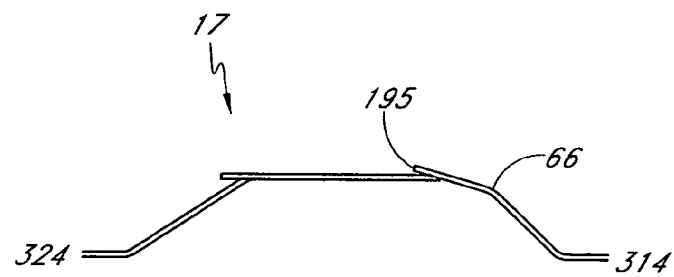
FIG. 4C is a schematic side view of the strut of FIG. 4B while collapsing, showing the position of a distal bend with reference to the distal anchor.
Figure 4D:
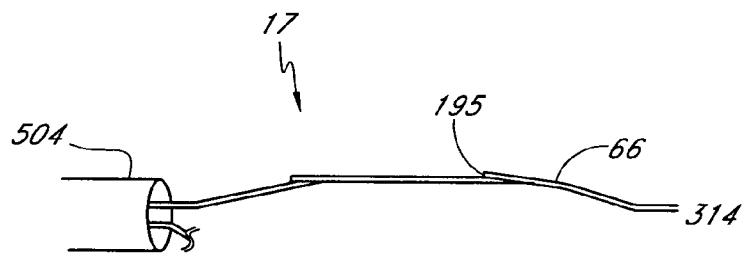
FIG. 4D is a schematic side view of the strut of FIG. 4B being drawn into a catheter, showing the position of a distal bend with reference to the distal anchor.
Figure 4F:
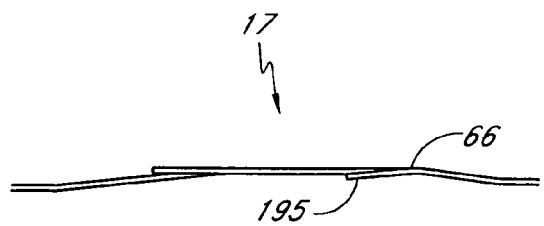
FIG. 4F is a schematic side view of the strut of FIG. 4B, showing the desired position of the distal anchor.

Referring to FIGS. 4A and 4B, a bend 66 is positioned just distal to a tissue anchor 195. FIG. 4E represents an enlarged perspective view of the distal bend 66 near the tissue anchor 195. FIGS. 4B, 4C, and 4D illustrate a series of conformations of a strut 17 in a frame 506 being collapsed for recapture into a catheter 504. The proximal hub 324 is located nearer the catheter 504, and the distal hub 314 is located farther from the catheter 504. When the frame is collapsed, the distal bend 66 has a levering effect, which may force the tissue anchor 195 downward into the native diameter as illustrated in FIG. 4F, facilitating recapture of the frame 506 into the catheter 504. Preferably, the distal bend 66 can force the tissue anchor 195 downward into the plane of strut 17 as illustrated in FIG. 4F, facilitating recapture of the frame 506 into the catheter 504. Preferably, the distal bend 66 can force the tissue anchor 195 downward into the plane of strut 17 as illustrated in FIG. 4E, facilitating recapture of the frame 506 into the catheter 504.

In one embodiment, where each strut includes a plurality of anchors 195, a single distal bend 66 on each strut is placed distal to the distalmost anchor. The distal bend 66 preferably has an aspect ratio less than that of the majority of the length of the strut, but greater than the aspect ratio of the bending region 23 adjacent the anchor. For example, where the majority of the strut 17 has an aspect ratio of about 2:1, and the bending region 23 has an aspect ratio of about 1:1, the distal bend 66 may have an aspect ratio of about 1.5:1. This distal bend 66 may be positioned about 2 mm distally to the anchor 195.

Figure 5:
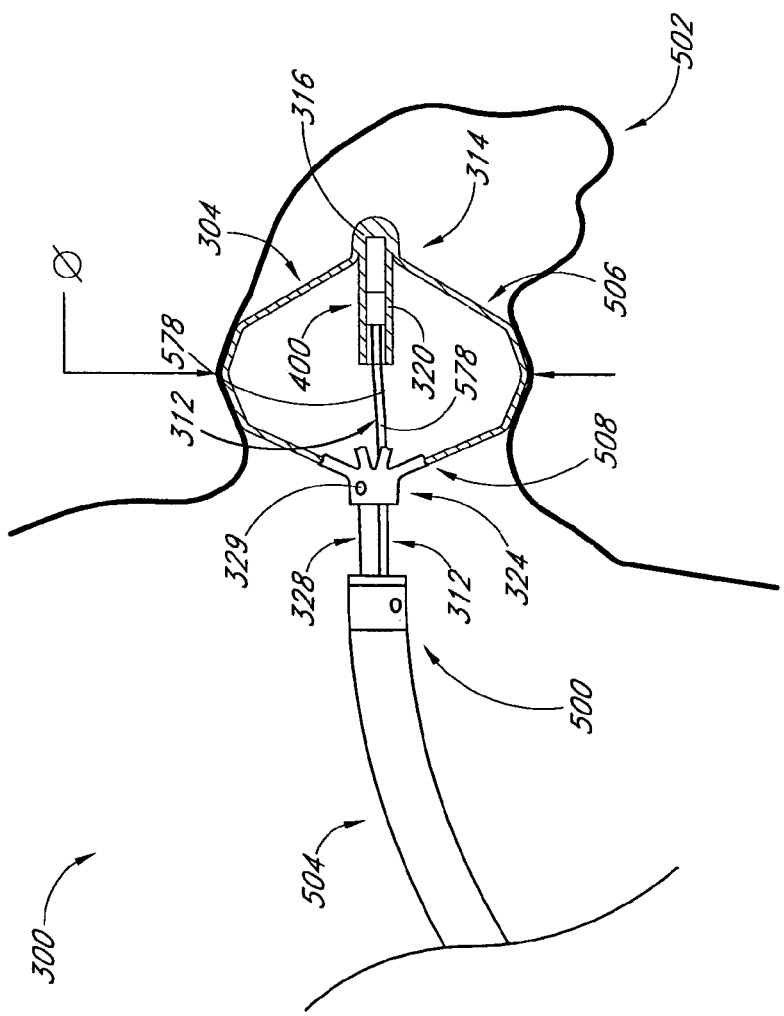
FIG. 5 is a schematic view of a deployment system delivering an implantable containment device to the left atrial appendage.

FIG. 5-13C illustrate a preferred system for delivering implants such as described above. FIG. 5 illustrates a deployment system 300, having an implant 304 and a delivery system 500, in accordance with one embodiment of the present invention. In a preferred embodiment, the implant 304 is a transluminally delivered device designed to occlude or contain particles within the left atrial appendage 502 (LAA 502) and prevent thrombus from forming in, and emboli from originating from, the LAA 502.

The delivery system 500 preferably may be used to deliver the implant 304 to occlude or block the LAA 502 in a patient with atrial fibrillation. The delivery system 500 preferably is compatible for use with a transseptal sheath 504, shown in FIGS. 13A-13C. The delivery system 500 and implant 304 preferably are designed to allow the implant 304 to be positioned, repositioned, and retrieved from the LAA 502 if necessary. Injection ports 546, 548, as shown in FIGS. 7 and 8, preferably are provided in the delivery system 500 to allow contrast injection proximally and distally of the implant 304 to facilitate in-vivo assessment of the positioning and seal quality of the implant 304.

Figure 6:
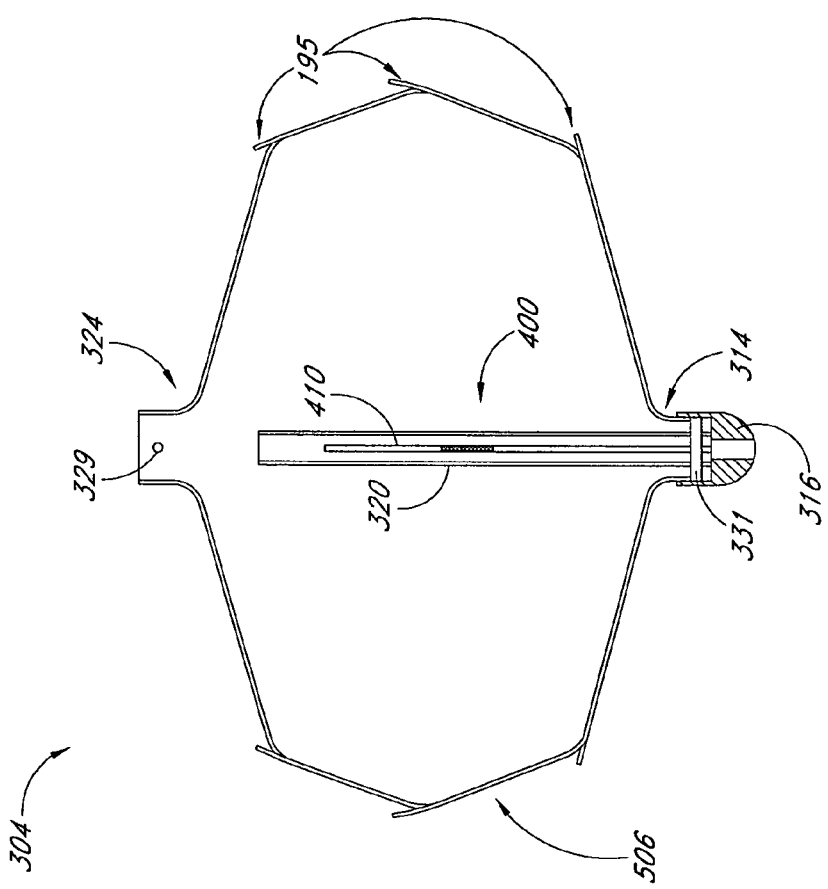
FIG. 6 is a schematic cross sectional view of an implantable containment device built in accordance with one embodiment of the present invention.

As shown in FIG. 6, the implant 304 preferably is available in a range of sizes to accommodate the anatomy of a patient's LAA 502. The implant 304 preferably comprises a frame 506 and a membrane (not shown) on a proximal face of the implant, such as described above. The frame 506 preferably is constructed of self-expanding nitinol supports. The membrane preferably is constructed of a fabric covering, such as one made of ePTFE, or an ePTFE/PE laminate. To attach the membrane to the frame 506, a PE mesh preferably is placed against the supports, with one sheet of ePTFE preferably placed over the PE mesh and another sheet of ePTFE preferably placed on an opposite side of the supports. The membrane preferably is heated on both sides causing the PE to melt into both sheets of ePTFE, thereby surrounding a portion of the frame 506. The nitinol supports allow the implant 304 to self-expand in the appendage 502, covering the orifice with the laminated fabric. The porous ePTFE/PE lamination facilitates rapid endothelialization and healing.

As shown in FIGS. 5 and 6, the implant 304 preferably extends from a proximal end or hub 324 to a distal end or hub 314. In some embodiments, the proximal hub 324 is coupled with a crosspin 329. In some embodiments the distal hub 314 is coupled with a slider assembly 400. The distal hub 314 preferably is coupled with an implant plug 316 in the distal hub 324. In one embodiment, the implant plug 316 comprises an atraumatic tip, such that contact between the atraumatic tip and the inside surface of the LAA 502 does not cause significant damage to the LAA 502. The implant 304 preferably is expandable and collapsible. The implant 304 preferably comprises anchors 195 that extend from the frame 506 when the implant 304 is expanded as described above. The distal hub 314 preferably comprises a cross pin 331, which is insertable through a hole 710 (FIGS. 2A-2D) in the distal hub 314. The proximal hub 324 preferably comprises a cross pin 329, which is insertable through a hole 709 (FIGS. 2A-2D) in the proximal hub 324.

Figure 8:
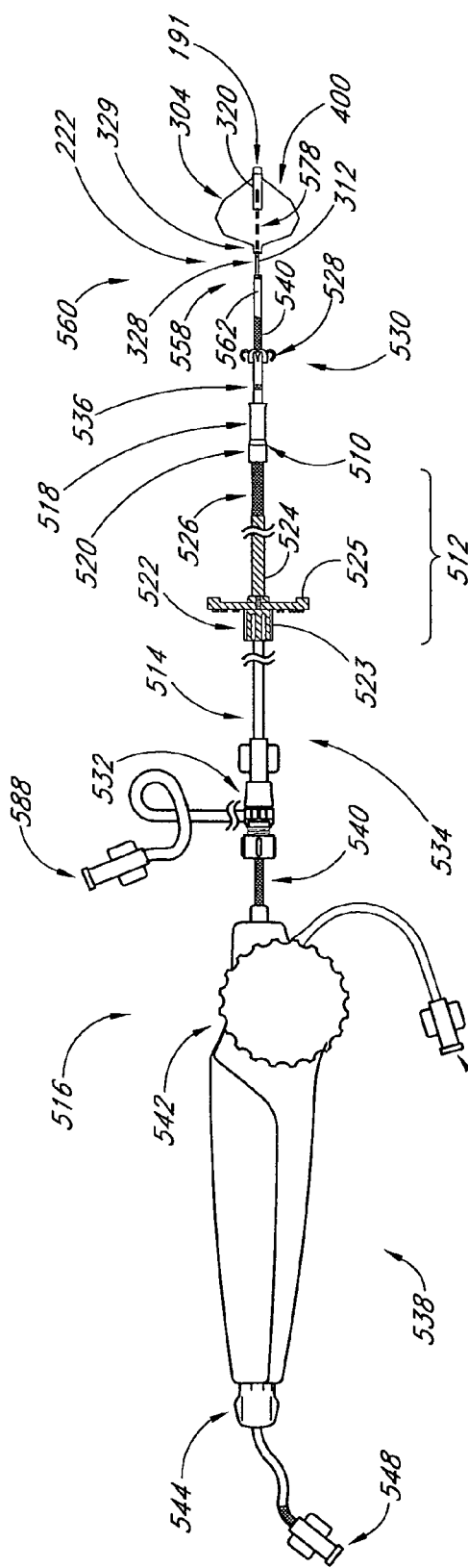
FIG. 8 is a schematic view of the delivery system of FIG. 7, shown attached to an implantable containment device.

As shown in FIGS. 7 and 8, the delivery system 500 preferably comprises a peel-away sheath 512, an optional recapture sheath 514, a deployment catheter 516, and an axially moveable core 312, each described further below. In addition, FIG. 7 illustrates the deployment system without a loading collar 510, and FIG. 8 illustrates the deployment system with a loading collar 510, with the system operably connected to an implant 304.

The deployment catheter 516 preferably comprises a deployment handle 538 and a multi-lumen shaft 540. As shown in FIGS. 7 and 8, the deployment handle 538 preferably comprises a control knob 542, a release knob 544, a proximal injection port 546 and a distal injection port 548. The multi-lumen shaft 540 preferably comprises a four-lumen shaft shown in FIG. 7A. The multi-lumen shaft 540 preferably comprises a core lumen 550 for holding an axially moveable core 312, a control line lumen 552 and two proximal injection lumens 554 in communication with proximal injection port 546.

Figure 11:
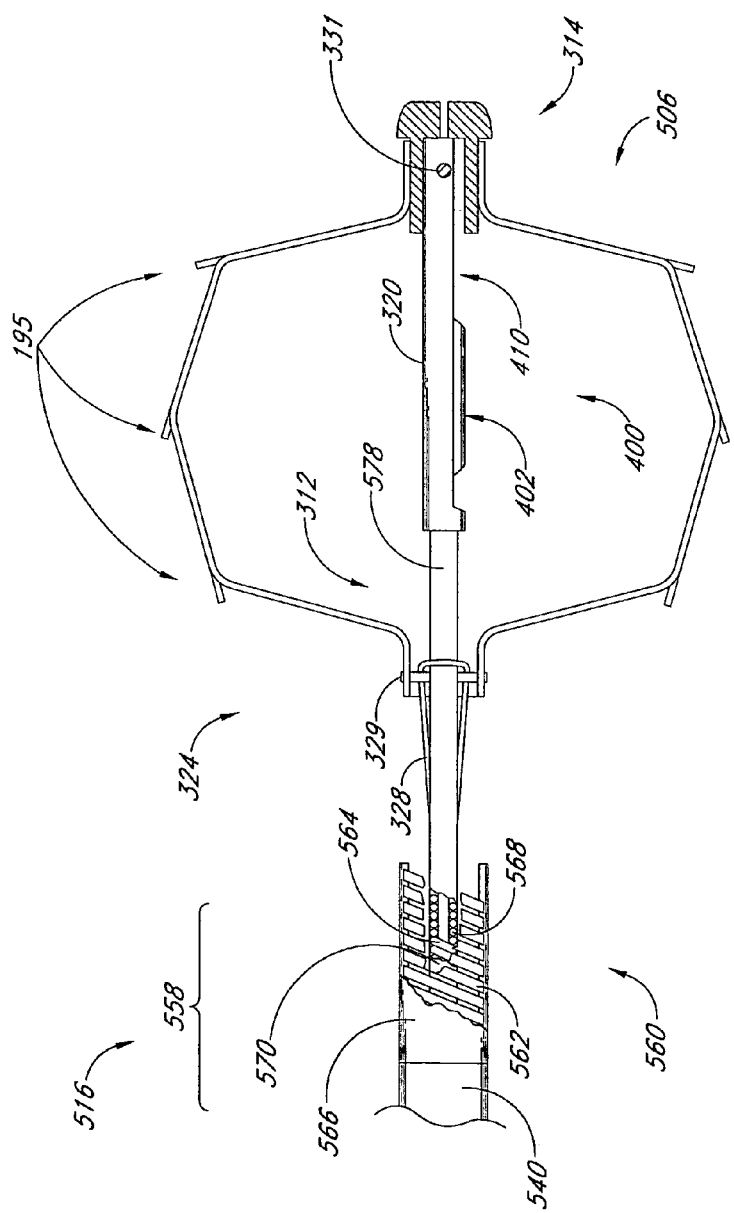
FIG. 11 is an enlarged partial cross sectional view of the deployment system of FIG. 7.

An axially moveable core 312 preferably extends from the deployment handle 538 through the core lumen 550 of the catheter 516 and couples the implant 304 to the delivery system 500 through a slider assembly 400. Referring to FIGS. 5, 8 and 11, a control line 328 preferably extends through the control line lumen 552 and preferably couples a proximal hub 324 of the implant 304 to the deployment handle control knob 542, allowing for implant 304 expansion and collapse. The control line 328 preferably extends around a portion of the axially movable core 312 near the proximal hub 324 of the implant 304, and is coupled to the implant 304 by a crosspin 329, as described above.

As shown in FIG. 11, the deployment catheter 516 preferably comprises a flexible catheter section 562 at its distal end, which in some embodiments is a spiral cut tubular section housed in a polymer sleeve 566. The flexible catheter section 562 may be coupled to a distal end of multilumen shaft 540.

As shown in FIGS. 11 and 12, the axially moveable core 312 preferably includes a hollow proximal shaft 576 and a hollow distal shaft 578 with a flexible hollow core section 564 therebetween, all co-axially aligned and connected. In one embodiment, the proximal end of the distal shaft 578 is attached to the distal end of the flexible core section 564, and the proximal end of the flexible core section 564 is attached to the distal end of the proximal shaft 576. In some embodiments, the flexible core section 564 has a spring coil section 568 housed in a polymer sleeve 570, the spring coil section 568 preferably coupled with the shafts 576 and 578 on first and second ends 572, 574.

The axially moveable core 312 preferably is disposed within the deployment catheter 516 such that the flexible core section 564 may be linearly co-located with the flexible catheter section 562 at a distal portion 560 of the delivery system 500 during appropriate times during a procedure, as shown in FIG. 11. When the flexible core section 564 is aligned and linearly co-located with the flexible catheter section 562, the sections preferably cooperate to form a delivery system flexible segment 558. As shown in FIGS. 7, 8, and 11, the delivery system flexible segment 558 preferably is located toward a distal end 560 of the delivery system 500.

In one embodiment, shown in FIG. 12, the distal shaft 578, flexible core section 564, and proximal shaft 576 are attached by welding. Small windows 580 may be provided to allow welding materials to flow between the shafts 564, 576 and 578 and provide stronger bonding therebetween. In another embodiment, solder, glue, or press-fitting is used to attach shafts 564, 576, and 578 to one another, as is well known to those of skill in the art. In another embodiment, the shafts 564, 576 and 578 are formed from a single tube, for example, a laser-cut tube. In other embodiments, more than one tube may be used to form each of the shafts 564, 576 and 578. For example, FIG. 12 illustrates proximal shaft 576 comprising two tubes connected by welding.

Referring to FIG. 12A, distal contrast media preferably can be injected through a lumen 582 in the shafts 576 and 578 for determining the placement of the implant 304. This lumen may be in fluid communication with distal injection port 548, shown in FIGS. 7 and 8. The distal shaft 578 preferably comprises a mating surface 584 and a radiopaque marker 586. In one embodiment, the mating surface 584 is a threaded surface. The distal shaft 578 preferably is releasably coupled through the implant 304 with a slider assembly 400.

Figure 10:
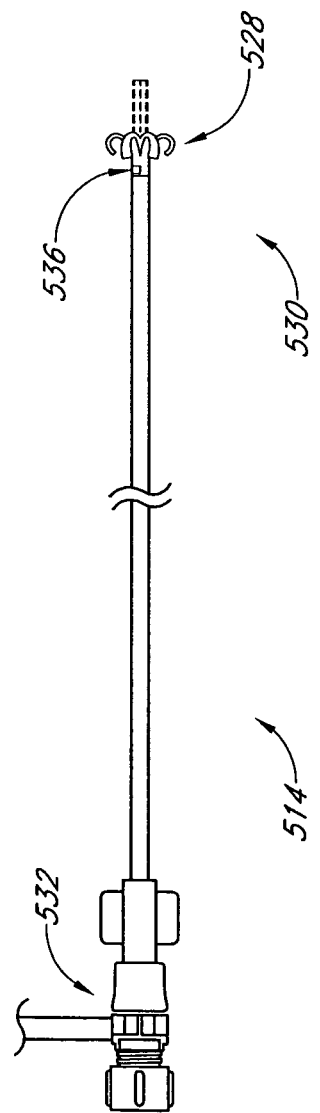
FIG. 10 is a schematic view of an optional recapture sheath used in the system of FIG. 7.

When the delivery system 500 is assembled, the optional recapture sheath 514 is preferably loaded over the deployment catheter 516, distal to the handle 538, as shown in FIGS. 7 and 8. The recapture sheath 514 preferably is designed to allow recapture of the implant 304 prior to its final release. Recapture petals or flares 528 preferably are provided on the distal end 530 of the recapture sheath 514, as illustrated in FIG. 10, to cover the anchors 195 of the implant 304 during retrieval into the transseptal sheath 504. A Touhy-Borst adapter or valve 532 preferably is attached to the proximal end 534 of the recapture sheath 514. The recapture sheath 514 preferably comprises a radiopaque marker 536 on its distal end 530 near the recapture flares 528. The recapture sheath 514 preferably comprises a recapture sheath injection port 588 for delivering fluid proximal the implant 304. In preferred embodiments, the recapture sheath and its associated components are optional.

The peel-away sheath 512 preferably is provided over a portion of the recapture sheath 514, between Touhy-Borst valve 532 and recapture flares 528. The peel-away sheath 512 preferably is used to introduce the delivery system 500 into a transseptal sheath 504 shown in FIGS. 13A-13C, described below. As shown in FIGS. 7 and 8, the peel-away sheath 512 preferably comprises a locking collar 522, a peel-away section 524, and a reinforced section 526. The locking collar can be unlocked relative to peel-away section 524, and preferably includes a threaded hub 523 that releasably engages tabs 525 of the peel-away section 524.

Figure 9:
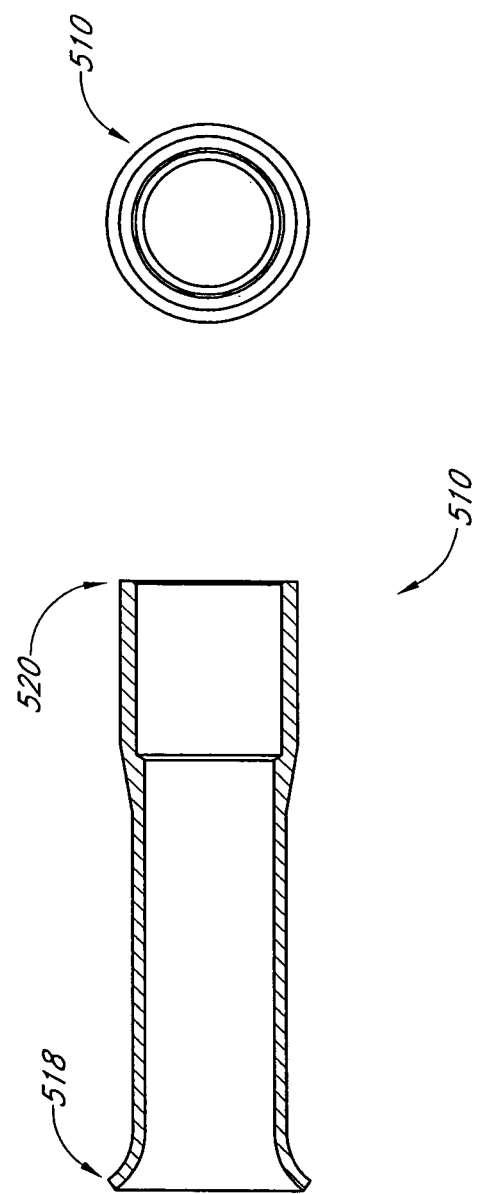
FIGS. 9A and 9B are a schematic cross sectional view and an end view, respectively, of a loading collar used in the system of FIG. 7.

The loading collar 510 preferably is located over a portion of the peel-away sheath 512 and a portion of the recapture sheath 514 with its proximal end being located over the peel-away sheath 512 and its distal end loaded over recapture sheath 514. The loading collar 510 preferably accommodates loading a collapsed implant 304 into the peel-away sheath 512 as described below. As shown in FIGS. 8 and 9, the loading collar 510 preferably comprises a first end portion 518 adapted to receive and extend over a collapsed implant 304, and a second end portion 520 configured to guide the collapsed implant 304 into the peel-away sheath 512. The loading collar 510 preferably is made of stainless steel.

To assemble the delivery system, the axially movable core 312 and control line 328 preferably are fed into the multi-lumen shaft 540 of the deployment catheter 516. The multi-lumen shaft 540 preferably is then coupled with components of the deployment handle 538 and the injection port components 546, 548. The peel-away sheath 512 and the loading collar 510 preferably are slid onto the recapture sheath 514, and the recapture sheath 514 is slid onto the deployment catheter 516. The implant 304 preferably is then loaded on an end of the axially movable core 312 and coupled with the control line 328. In one embodiment, the implant 304 is loaded on an end of the axially movable core 312 by screwing the axially movable core 312 into the slider nut 402 of the slider assembly 400. The control knob 542 and outer casing of the deployment handle 538 preferably are then coupled with the system.

The deployment system 300 preferably is used in connection with a transseptal sheath 504 to advance the implant 304 for deployment in a patient. As shown in FIGS. 5 and 13A-13C, the transseptal sheath 504 is a tubular device that in one embodiment can be advanced over a guidewire (not shown) for accessing the LAA 502 of a patient. Transseptal sheath 504 in one embodiment has a permanent bend 594, as shown in the views of FIGS. 13A and 13B. A hemostasis valve 596 is provided at the proximal end of transseptal sheath. A fluid injection port 598 is also provided at the proximal end to deliver fluid such as contrast media through the transseptal sheath. Systems and methods for implanting the device 304 in the LAA 502 are described further below.

In one embodiment, the system and method preferably allows for access and assessment of the LAA 502. A guidewire (not shown) preferably is used to access the superior vena cava through groin access. A transseptal sheath 504 preferably is advanced over the guidewire and into the superior vena cava. The guidewire preferably is removed and replaced with a transseptal needle (not shown). The transseptal sheath 504 preferably is retracted inferiorly so that the bend 594 in transseptal sheath directs the distal tip of the transseptal sheath toward the fossa ovalis. The needle preferably is advanced to puncture the fossa ovalis. The transseptal sheath 504 preferably is advanced to establish access to the LAA 502 and the needle preferably is retracted. Further details and disclosure are provided in copending U.S. patent application Ser. No. 09/435,562, filed Nov. 8, 1999, and U.S. Patent Application Publication No. 2002-0111647, the entireties of which are hereby incorporated by reference.

After properly preparing a transseptal sheath 504 for LAA 502 access, the size of the neck diameter and morphology of the LAA 502 preferably is determined by advancing the transseptal sheath 504 to the distal portion of the LAA 502 and injecting contrast media to obtain an initial left atrial appendogram. The neck diameter preferably is measured approximately 5 mm in from the ostium of the LAA 502 at end diastole.

In one embodiment, the system and method preferably allows for selection and preparation of a deployment system 300. A deployment system 300 preferably comprises an implant 304 of an appropriate size for placement in a patient. Initially, the implant 304 preferably is in an expanded configuration, with axially moveable core 312 engaging slider assembly 400, as described above. The recapture sheath 514 preferably is positioned so it covers and supports the flexible segment 558 of the delivery system 500, wherein the flexible catheter section 562 of deployment catheter 302 and flexible core section 564 of axially moveable core 312 are aligned.

The Touhy-Borst valve 532 preferably is tightened over the deployment catheter 516 to prevent relative movement between recapture sheath 514 and deployment catheter 516. The loading collar 510 and peel-away sheath 512 preferably are positioned so they are at the base of the recapture flares 528, proximal thereto.

The delivery system 500 preferably is loaded by rotating the control knob 542 counterclockwise until the implant 304 is fully collapsed. Preferably, at least a portion of the control line 328 is coupled with the control knob 542 such that rotation of the control knob 542 in the counterclockwise direction retracts at least a portion of the control line 328. Retraction of the control line 328 preferably places tension on the proximal hub 324 of the implant 304, because a portion of the control line 328 preferably is coupled with the proximal hub 324 by a pin 329. While the distal portion of the axially moveable core 312 engages slider assembly 400 and applies a distal force to distal hub 314 of the implant 304, tension in the control line 328 preferably causes the proximal hub 324 of the implant 304 to move proximally relative the axially moveable core 312, thereby collapsing the implant 304.

The diameter of the implant 304 preferably is reduced to approximately $\frac{1}{3}^{rd}$ or less of its original diameter when collapsed. The loading collar 510 and peel-away sheath 512 are then advanced distally over the flares 528 and implant 304 until the distal tip of the implant 304 is aligned with the distal end of the peel-away sheath 512 and the distal end of the loading collar is about 1.5 cm from the distal tip of the implant. At this point, the flares 528 partially cover the implant. The loading collar 510 preferably is removed and discarded.

With the implant 304 partially within the recapture sheath 514 and retracted within the peel-away sheath 512, the entire system preferably is flushed with sterile heparinized saline after attaching stopcocks to the recapture sheath injection port 588, the proximal injection port 546 and distal injection port 548 of the delivery system 500. The recapture sheath 514 and the Touhy-Borst valve 532 are first thoroughly flushed through port 588. Then the distal injection port 548 and the proximal injection port 546 of the deployment handle 538 are preferably flushed through. The distal injection port 548 is in fluid communication with lumen 426 of axially moveable core 312, and proximal injection port 546 is in fluid communication with injection lumens 554 of multilumen shaft 540. The transseptal sheath 504 placement preferably is reconfirmed using fluoroscopy and contrast media injection.

The delivery system 500, as described above, with implant 304 inserted therein, preferably is then inserted into the proximal end of the transseptal sheath 504. To avoid introducing air into the transseptal sheath 504 during insertion of the delivery system 500, a continual, slow flush of sterile heparinized saline preferably is applied through the proximal injection port 546 of the deployment handle 538 to the distal end of the deployment catheter 516 until the tip of the peel-away sheath 512 has been inserted into, and stops in, the hemostatic valve of the transseptal sheath 504. Preferably, the distal tip of the peel-away sheath 512 is inserted approximately 5 mm relative to the proximal end of the transseptal sheath 504.

Under fluoroscopy, the recapture sheath 514 and deployment catheter 516 preferably are advanced, relative to the peel-away sheath 512, approximately 20-30 cm from the proximal end of the transseptal sheath, and the system 500 preferably is evaluated for trapped air. The peel-away sheath 512 is preferably not advanced into the transseptal sheath 504 due to the hemostasis valve 596 blocking its passage. If air is present in the system 500, it may be removed by aspirating through the distal injection port 548, recapture sheath injection port 588, or proximal injection port 546. If air cannot be aspirated, the deployment catheter 516 and recapture sheath 514 preferably are moved proximally and the delivery system 500 preferably is removed from the transseptal sheath 504. All air preferably is aspirated and the flushing/introduction procedure preferably is repeated.

The peel-away sheath 512 preferably is manually slid proximally to the proximal end 534 of the recapture sheath 514. The Touhy-Borst valve 532 preferably is loosened and the deployment catheter 516 preferably is advanced distally relative to the recapture sheath 514 until the deployment handle 538 is within about 2 cm of the Touhy-Borst valve 532 of the recapture sheath 514. This causes the implant 304 to be advanced distally within the transseptal sheath 504 such that the recapture sheath 514 no longer covers the implant 304 or the flexible section 558. The Touhy-Borst valve 532 preferably is tightened to secure the deployment catheter 516 to fix relative movement between the deployment catheter 516 and recapture sheath 514.

Under fluoroscopy, the implant 304 preferably is advanced to the tip of the transseptal sheath 504 by distal movement of the delivery catheter 302. The distal hub 314 of implant 304 preferably is aligned with a transseptal sheath tip radiopaque marker 590. Under fluoroscopy, the sheath 504 positioning within the LAA 502 preferably is confirmed with a distal contrast media injection.

The position of the implant 304 preferably is maintained by holding the deployment handle 538 stable. The transseptal sheath 504 preferably is withdrawn proximally until its tip radiopaque marker 590 is aligned with the distal end of the deployment catheter flexible segment 558. This preferably exposes the implant 304.

Under fluoroscopy, the implant 304 preferably is expanded by rotating the control knob 542 clockwise until it stops. Rotating the control knob 542 preferably releases tension on the control line 328, preferably allowing the implant 304 to expand. The implant 304 preferably is self-expanding. After expansion, any tension on the LAA 502 preferably is removed by carefully retracting the deployment handle 538 under fluoroscopy until the radiopaque marker 586 on the axially movable core 312 moves proximally approximately 1-2 mm in the guide tube 320. The position of the implant 304 relative the LAA 502 preferably is not altered because the axially movable core 312 preferably is coupled with the slider assembly 400 allowing for relative movement between the implant 304 and the axially movable core 312. The slider assembly 400 preferably allows for the distal portion of the axially movable core 312 to be slightly retracted proximally from the distal hub 314 of the implant 304, thereby removing any axial tension that may be acting on the implant 304 through the axially movable core 312. The radiopaque marker 586 preferably is about 1-2 mm proximal from the implant 304 distal hub 314, and the transseptal sheath 592 tip preferably is about 2-3 mm proximal from the implant proximal hub 324, thereby indicating a neutral position.

Under fluoroscopy, the expanded diameter (Ø in FIG. 5) of the implant 304 preferably is measured in at least two views to assess the position of the implant within the LAA 502. The measured implant diameter Ø preferably is compared to the maximum expanded diameter.

Preferably, the labeled proximal and distal injection ports 546, 548 of the deployment handle 538 shown in FIG. 7, correlate with the proximal and distal contrast media injections. The proximal contrast media injections are delivered through the delivery catheter lumen 554 to a location proximal to the implant 304. The distal contrast media injections are delivered through the axially movable core 312 to a location distal to the implant 304. Proximal contrast media injections preferably are completed in two views. If the injection rate is insufficient, the recapture sheath injection port 588 may be used independently or in conjunction with the proximal injection port 546 to deliver fluid to a location proximal to the implant 304.

If satisfactory results are seen, any transverse tension on the LAA 502 preferably is released by exposing the flexible segment 558 of the delivery system 500. The flexible catheter section 562 and the flexible core section 564 preferably are linearly co-located to cooperate as the flexible segment 558 of the delivery system 500. This preferably is accomplished by retracting the transseptal sheath 504 proximally approximately 2 cm to expose the flexible segment. By exposing the flexible segment 558, the flexible segment 558 preferably will flex to allow the implant 304 to sit within the LAA 502 free from transverse forces that may be created, for example, by contractions of the heart acting against the transseptal sheath 504 or deployment catheter 516.

Once the flexible segment 558 is exposed, distal contrast media injections preferably are completed in at least two views to verify proper positioning of the implant 304. A flush of saline preferably is used as needed between injections to clear the contrast media from the LAA 502. Following the contrast media injections, the transseptal sheath 504 preferably is advanced distally to cover the flexible segment 558.

If implant 304 position or results are sub-optimal, the implant 304 preferably may be collapsed and repositioned in the LAA 502. To achieve this, under fluoroscopy, the deployment handle 538 preferably is advanced distally to place the radiopaque marker 586 of the axially moveable core 312 at the distal hub 314 of the implant 304. The distal end of the transseptal sheath 504 preferably is aligned with the distal end of the flexible segment 558. The control knob 542 preferably is rotated until the implant 304 has been collapsed to approximately $\frac{1}{3}^{rd}$ or less of its expanded diameter. The control knob 542 preferably acts on the control line 328 to place tension on the proximal hub 324 of the implant 304, pulling the proximal hub 324 of the implant 304 proximally relative the distal hub 314 of the implant 304 to collapse the implant 304. The implant 304 preferably can be repositioned and re-expanded.

The stability of the implant 304 preferably is verified in several views. Stability tests preferably are preformed in the following manner. A contrast media filled syringe preferably is connected to the distal injection port 548 of the deployment handle 538. Under fluoroscopy, at least about a 10 mm gap between the tip of the transseptal sheath 504 and the proximal hub 222 of the implant 304 is preferably confirmed.

The stability of the implant 304 in the LAA 502 preferably is evaluated using fluoroscopy and echocardiography. The recapture sheath Touhy-Borst valve 532 preferably is loosened. Then the deployment handle 538 preferably is alternately retracted and advanced about 5-10 mm while maintaining the position of the transseptal sheath 504 and simultaneously injecting contrast media through the distal injection port 548. This tests how well the implant is held within the LAA 502.

If the implant stability tests are unacceptable, the implant 304 preferably may be collapsed and repositioned as described above. If repositioning the implant 304 does not achieve an acceptable result, the implant 304 preferably may be collapsed and recaptured as described further below.

The implant 304 preferably meets the following acceptance criteria, associated with the assessment techniques listed below, prior to being released. The assessment techniques to be evaluated preferably include 1) residual compression; 2) implant location; 3) anchor engagement; 4) seal quality; and 5) stability. For residual compression, the implant diameter Ø, as measured by fluoroscopic imaging, preferably is less than the maximum expanded diameter of the implant 304. For implant location, the proximal sealing surface of the implant 304 preferably is positioned between the LAA 502 ostium and sources of thrombus formation (pectinates, secondary lobes, etc.) (preferably imaged in at least two views). For anchor engagement, the implant frame 506 preferably is positioned within the LAA 502 so as to completely engage a middle row of anchors 195 in an LAA 502 wall (preferably imaged in at least two views). For seal quality, the contrast injections preferably show leakage rated no worse than mild (preferably defined as a flow of contrast media, well defined, and filling one-third of the LAA 502 during a proximal injection over a period of up to about five ventricular beats, preferably imaged in at least two views). For stability, there preferably is no migration or movement of the implant 304 relative to the LAA 502 wall as a result of the Stability Test.

If implant recapture is necessary, because a different size implant 304 is necessary or desired, or if acceptable positioning sealing cannot be achieved, the implant 304 preferably is fully collapsed as described above. Once the implant 304 is collapsed, the locking collar 522 of the peel away sheath 512 preferably is unlocked. The peel-away portion 524 of the peel-away sheath 512 preferably is split up to the reinforced section 526 and removed. The reinforced section 526 of the peel-away sheath 512 preferably is slid proximally to the hub of the recapture sheath 514. The Touhy-Borst valve 532 on the proximal end of the recapture sheath 514 preferably is slightly loosened to allow smooth movement of the sheath 514 over deployment catheter 516 without allowing air to enter past the Touhy-Borst valve 532 seal. By removing the peel-away portion 524 of peel-away sheath 512, the recapture sheath 514 can now be advanced further distally relative to the transseptal sheath.

While holding the deployment catheter 516 and transseptal sheath 504 in place, the recapture sheath 514 preferably is advanced distally into the transseptal sheath 504 until a half marker band 536 on the recapture sheath 514 is aligned with a full marker band 590 on the transseptal sheath 504. This preferably exposes the recapture flares 528 outside the transseptal sheath.

The collapsed implant 304 preferably is retracted into the recapture sheath 514 by simultaneously pulling the deployment handle 538 and maintaining the position of the recapture sheath 514 until approximately half the implant 304 is seated in the recapture sheath 514. The Touhy-Borst valve 532 on the recapture sheath 514 preferably is tightened over the deployment catheter 516. The recapture sheath 514 and implant 304 preferably are retracted into the transseptal sheath 504 by pulling on the recapture sheath 514 while maintaining the position of the transseptal sheath 504, preferably maintaining left atrial access. The recapture flares 528 of the recapture sheath 514 preferably cover at least some of the anchor elements 195 on the implant 304 as the implant is retracted proximally into the transseptal sheath 504. It will be appreciated that because preferred embodiments of the implant as described above may advantageously position the anchors within or even below the collapsed diameter of the implant, retrieval of the implant may be accomplished without using the recapture sheath as described herein.

If the implant's position and function are acceptable, and implant recapture is not necessary, the implant 304 preferably is released from the delivery system 500. Under fluoroscopy, the transseptal sheath 504 preferably is advanced to the proximal hub 324 of the implant 304 for support. The release knob 544 on the proximal end of the deployment handle 538 preferably is rotated to release the implant 304. Rotating the release knob 544 preferably causes a threaded portion 584 of the distal shaft 578 of the axially movable core 312 to rotate with respect to the slider assembly 400 such that the threaded section 584 preferably is decoupled from the slider assembly 400. Under fluoroscopy, after the axially movable core 312 is decoupled from the implant 304, the release knob 544 preferably is retracted until the distal end 578 of the axially movable core 312 is at least about 2 cm within the transseptal sheath 504.

Figure 16:
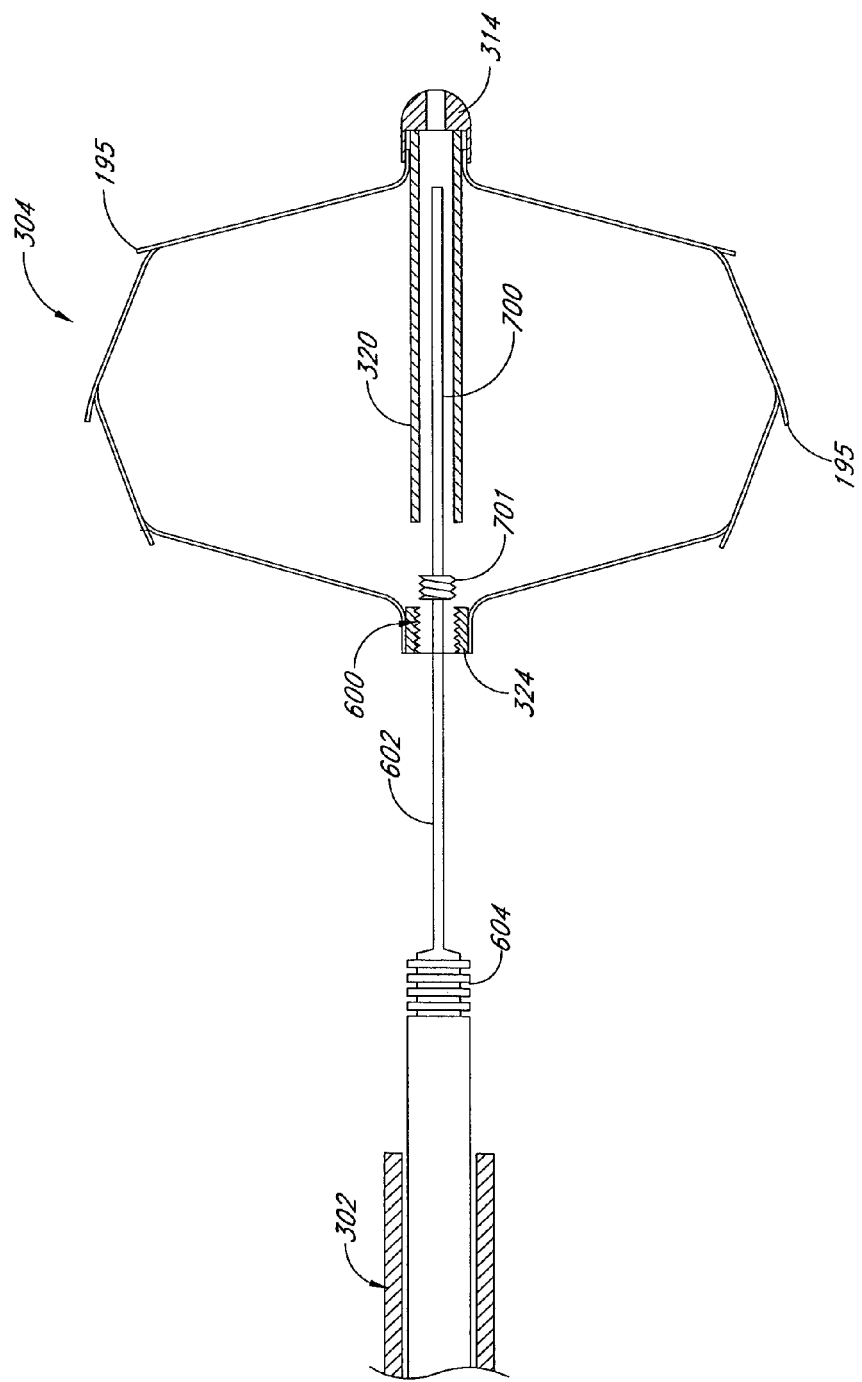
FIG. 16 is a schematic view of a delivery system constructed in accordance with one embodiment of the present invention.

Another preferred embodiment of the present invention comprises an implant and delivery system as illustrated in FIGS. 14-16. In the preferred embodiment of FIG. 14, the implant 304 has a proximal hub 324 with internal threads 600 and a distal hub 314 with an optional central hole 601 for slideably receiving a guidewire (not shown). The internal threads 600 of the proximal hub 324 mate with the external threads 603 of the distal end of the delivery wire 602.

The delivery wire 602 is comprised preferably of metal and is typically about 175 cm long. The delivery wire 602 is attached to the implant 304 by means of threaded connections 600 and 603, and is used to pull the implant 304 into the delivery catheter 302 and to expel the implant 304 from the delivery catheter 302. The delivery wire 602 may comprise a flexible segment 604 made, for example, by thinning the delivery wire 602, cutting partial thickness grooves or slots into the wire 602, or other means as commonly known in the art. Flexible segment 604 allows the implant 304 to be implanted in the body with the implant position relatively unencumbered by the delivery wire's 602 stiffness. The implant 304 so implanted can thus be observed in a near final implanted position without detaching the delivery wire 602. If the implant 304 is not in proper position it can be retracted into delivery catheter 302, repositioned, and redeployed.

As illustrated in FIG. 15, the delivery wire 602 can be hollow. Hollow delivery wires 602 can be used over a guidewire (not shown), wherein the guidewire preferably passes through a hole in the distal hub 314. The hollow delivery wire 602 can also be used for injection of contrast, preferably into central portion of implant 304, so that contrast leakage from the atrial appendage can be evaluated prior to detachment of the implanted implant 304 from the delivery wire 602. Flexible segment 604 (not shown in FIG. 15) may be made from cutting slots or spiral slots, of full or partial thickness, into a tube and is preferably substantially fluid tight to keep contrast from exiting the flexible segment 604 of the hollow delivery wire 602. The flexible segment 604 may be coated with a fluid tight casing such as a polyethylene, PEBAX, urethane, or other polymer film. Alternatively, the slots in flexible segment 604 may be filled with flexible materials.

In FIG. 15, the delivery catheter 302 is preferably a tube, approximately 150 cm long. The delivery wire 602 is slideably received by the delivery catheter 302. The delivery catheter 302 preferably comprises a flexible segment (not shown) of a more flexible polymer of slots, grooves, or other formation known to those skilled in the art. In FIG. 14, the flexible segment 604 of delivery catheter 302 preferable overlaps the flexible segment 604 of the delivery wire 602 during evaluation of the implant position and function following implant deployment.

In use, the preferred embodiments of the implant 304 can preferably be deployed or recovered using a simple delivery system comprising delivery wire 602 in combination with delivery catheter 302, because the anchors 195 on implant 304 preferentially pronate such that they do not 'catch' on the delivery catheter 302 during implant recovery or implant delivery. In one embodiment anchors 195 move into the plane of strut 17 (see FIG. 4D) during withdrawal of implant into catheter 302, thereby preventing anchor 195 from contacting distal end of catheter 302 and impeding withdrawal of implant into catheter 302. In another embodiment anchors 195 move inward to the plane of strut 17 (see FIG. 4F) during withdrawal of implant into catheter 302.

Figure 17:
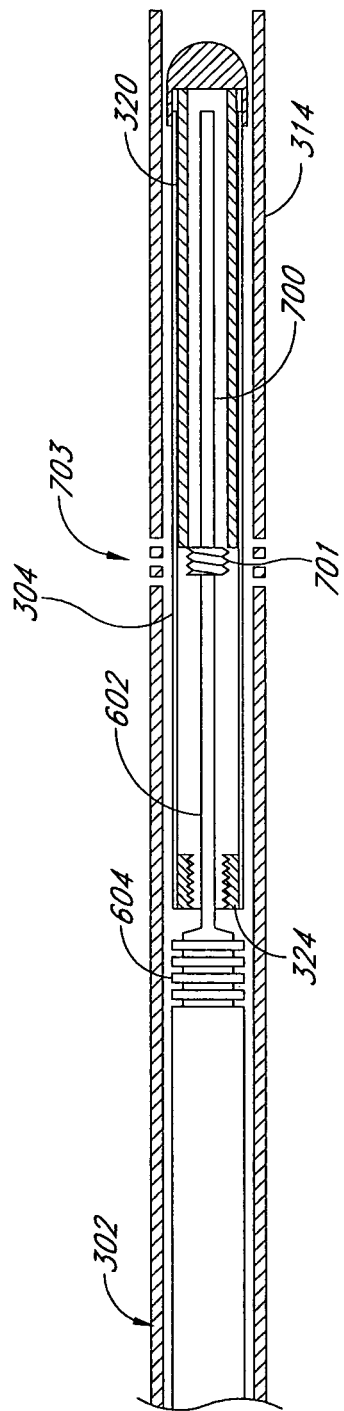
FIG. 17 is a is a schematic view of the delivery system of FIG. 16, showing the delivery wire and device contained within the delivery catheter.
Figure 18:
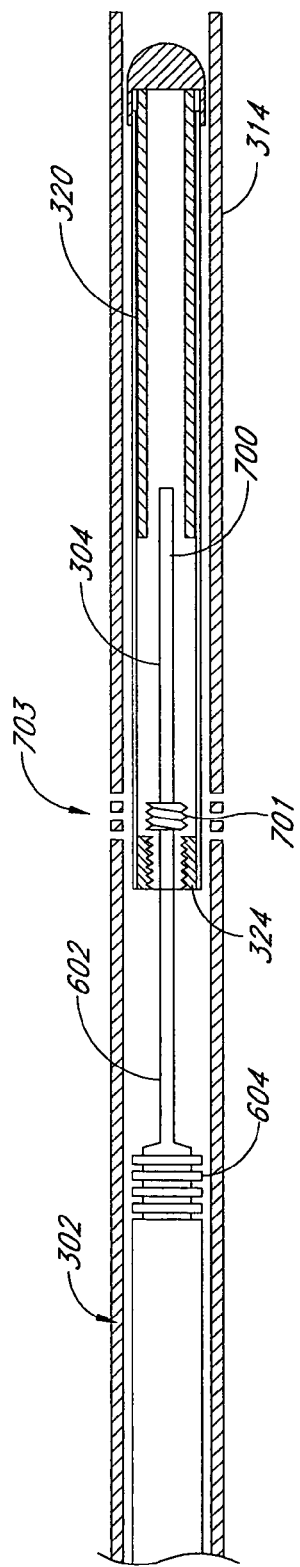
FIG. 18 is a is a schematic view of a the delivery system of FIG. 16, showing the delivery wire and implant device contained and lengthened within the delivery catheter.

FIGS. 16-18 illustrate further preferred embodiments of implants and delivery systems of the present invention.

As illustrated in FIG. 16, the implant 304 has a proximal hub 324 with internal threads 600 and distal hub 314 with a guide tube 320 for slideably receiving the end portion 700 of the delivery wire 602. The internal threads 600 of proximal hub 324 mate with external threads of stop 701 on the delivery wire 602.

The delivery wire 602 preferably comprises metal and is typically 175 cm long. The delivery wire 602 is slideably attached to the implant 304 by means of threaded stop 701, threaded proximal hub 324, and guide tube 320. The delivery wire 602 is preferably used to pull implant 304 into the delivery catheter 302 and to expel the implant 304 from the delivery catheter 302. The delivery wire may comprise flexible segment 604 made, for example, by thinning wire, cutting partial thickness grooves or slots into wire, or other means as commonly known in the art. Flexible segment 604 allows implant 304 to be implanted in the body with the implant position relatively unencumbered by stiffness of the delivery wire 602. The implant 304 so implanted can thus be observed in a near final implanted position without detaching delivery wire 602. If the implant is not in proper position it can be retracted into delivery catheter 302, repositioned, and redeployed.

As illustrated in FIG. 17, the delivery catheter is preferably a tube, approximately 150 cm long, wherein the delivery wire 602 is slideably received therein. The delivery catheter 302 preferably comprises a flexible segment 703 of a more flexible polymer of slots, grooves, or other shape known to those skilled in the art. The flexible segment 703 of delivery catheter 302 preferable overlaps the flexible segment 604 of delivery wire 602 during evaluation of implant position and function following implant deployment.

In use, implant 304 can be delivered and recovered with less force and smaller catheter diameters than prior art approaches. During delivery, the end portion 700 or stop 701 of the delivery wire 602 will push on the distal hub 314 or guide tube 320 respectively and lengthen the implant 304, thereby reducing the implant diameter and the force of the implant against the inner walls of delivery catheter 302. In FIG. 18, during recovery, threaded stop 701 will abut proximal hub 324 and lengthen the implant 304, thereby reducing the implant diameter and the force of the implant 304 against the inner walls of delivery catheter 302. After implantation, stop 701 can be retracted to contact proximal hub 324, and unthreaded through proximal hub 324, thereby freeing delivery wire 602 from implant 304. A similar mechanism is disclosed in EP 1 210 032, which is hereby incorporated in its entirety by reference herein.

In use, the implant 304 can be deployed or recovered using simple a delivery system which combines deployment catheter 302 and the delivery wire 602, because the anchors 195 on the implant 304 preferentially pronate such that they do not "catch" on the delivery catheter 302 during implant recovery or implant delivery. In one embodiment anchors 195 move into the plane of strut 17 (see FIG. 4D) during withdrawal of implant into catheter 302, thereby preventing anchor 195 from contacting distal end of catheter 302 and impeding withdrawal of implant into catheter 302. In another embodiment anchors 195 move inward to the plane of strut 17 (see FIG. 4F) during withdrawal of implant into catheter 302.

Under fluoroscopy, while assuring that transseptal access is maintained, the delivery system 500 preferably is retracted and removed through the transseptal sheath 504. Under fluoroscopy, the transseptal sheath 504 position preferably is verified to be approximately 1 cm away from the face of the implant 304. Contrast injections, fluoroscopy and/or echocardiography preferably may be used to confirm proper positioning and delivery of the implant 304 and containment of the LAA 502. The transseptal sheath 504 preferably is withdrawn.

Throughout this application the terms implant and occlusion device have been used. One of ordinary skill in the art will appreciate that all of the disclosures herein are applicable to a wide variety of structures that include both implants that may or may not also be occlusion devices. Routine experimentation will demonstrate those limited circumstances under which certain disclosures and combinations thereof are not beneficial.

Further details regarding left atrial appendages devices and related methods are disclosed in U.S. Pat. No. 6,152,144, titled "Method and Device for Left Atrial Appendage Occlusion," filed Nov. 6, 1998, U.S. patent application Ser. No. 09/435,562, filed Nov. 8, 1999, and U.S. Patent Application Publication No. 2002/0111647, titled "Method and Device for Left Atrial Appendage Occlusion," filed Oct. 19, 2001. The entirety of each of these is hereby incorporated by reference.

While particular forms of the invention have been described, it will be apparent that various modifications can be made without departing from the spirit and scope of the invention. Accordingly, it is not intended that the invention be limited, except as by the appended claims.

What is claimed is:

1. An embolic containment device, comprising:
    an expandable frame that is moveable between a collapsed configuration and an expanded configuration, the expandable frame having a proximal hub and a distal hub;
    a plurality of supports each having a jogged portion and a length extending between the proximal hub and the distal hub, the length defining a longitudinal axis of each support when the frame is in the collapsed configuration, wherein the support extends continuously from the proximal hub of the frame to the distal hub of the frame through the jogged portion; and
    a plurality of tissue anchors integrally formed and attached to supports, said anchors extending alongside a portion of said supports and having tissue engagement ends extending, when the frame is in the collapsed configuration, outwardly beyond an outer surface of the expandable frame and generally toward the proximal hub;
    wherein the supports have an aspect ratio that decreases in said portion alongside said anchors to form a bending region of said supports, and said anchors are attached proximal to a jogged portion along the length of a corresponding support, said jogged portion turning at least partially laterally away from the longitudinal axis of said support when the frame is in the collapsed configuration.

2. The device of claim 1, further including a barrier provided on at least a proximal face of the frame.

3. The device of claim 1, wherein the plurality of tissue anchors includes a proximal anchor, an intermediate anchor, and a distal anchor attached to each of the plurality of supports.

4. The device of claim 1, wherein the frame in the expanded configuration has a generally spherical shape.

5. The device of claim 1, wherein the frame is self-expanding.

6. The embolic containment device of claim 1, wherein the device is configured for containing embolic material with an atrial appendage of a patient.

7. An implantable device, comprising:
an expandable frame that is moveable between a collapsed configuration and an expanded configuration, the expandable frame having a proximal end and a distal end;
a plurality of supports, each of the plurality of supports having a jogged portion and a length that extends at least partially between the proximal end and the distal end of the frame, the length defining a longitudinal axis of each of the plurality of supports when the frame is in the collapsed configuration; and
a plurality of tissue anchors attached to each of the plurality of supports, each tissue anchor of the plurality of tissue anchors having tissue engagement ends, the tissue engagement ends extending outwardly beyond an outer surface of the expandable frame and generally toward the proximal end of the frame when the frame is in the collapsed configuration; and
wherein each of the plurality of supports has at least a first bending region spaced laterally from one of the plurality of tissue anchors and a second bending region spaced distally from the one of the plurality of tissue anchors, said second bending region having an aspect ratio greater than that of the first bending region, and wherein said first and second bending regions have smaller aspect ratios than an aspect ratio of a portion of each of the plurality of supports that extends between said first and second bending regions.

8. The device of claim 7, wherein the plurality of tissue anchors includes a proximal anchor, an intermediate anchor, and a distal anchor.

9. The device of claim 7, wherein the each of the plurality of tissue anchors is integrally formed with the one of the plurality of supports.

10. A defect closure device, comprising:
an expandable frame that is moveable between a collapsed configuration and an expanded configuration sized to fit within the defect, the expandable frame having a proximal hub and a distal hub;
a plurality of supports each having a jogged portion and a length extending between the proximal hub and the distal hub, the length defining a longitudinal axis of each support when the frame is in the collapsed configuration, wherein the supports extend continuously from the proximal hub of the frame to the distal hub of the frame through the jogged portions; and
a plurality of tissue anchors integrally formed and attached to supports, wherein when the expandable frame is in the collapsed configuration, said anchors extend outwardly beyond an outer surface of the expandable frame and alongside a portion of said supports, the anchors having tissue engagement ends;
wherein the supports have an aspect ratio that decreases in said portion alongside said anchors to form a bending region of said supports, and said anchors are attached adjacent to a jogged portion along the length of a corresponding support, said jogged portion turning at least partially laterally away from the longitudinal axis of said support when the frame is in the collapsed configuration.

11. The defect closure device of claim 10, wherein the expandable frame is sized and configured for placement within a septal defect.

12. The defect closure device of claim 10, wherein the expandable frame is sized and configured for placement within a patent foramen ovale.

13. The defect closure device of claim 10, wherein the expandable frame is sized and configured for placement within a patent ductus arteriosus.

14. An implantable device, comprising:
an expandable frame that is moveable between a collapsed configuration and an expanded configuration;
a plurality of supports, each of the plurality of supports having at least one strut with a first aspect ratio and a bending region with a second aspect ratio that is different from the first aspect ratio, each of the plurality of supports having a jogged portion that extends at least partially laterally away from the at least one strut in the collapsed configuration;
a plurality of anchors attached to a respective one of the plurality of supports, the plurality of anchors including an intermediate anchor, a distal anchor, and a proximal anchor, the intermediate anchor positioned between the proximal anchor and the distal anchor on the respective one of the plurality of supports, the intermediate anchor attached to the respective one of the plurality of supports adjacent to the jogged portion.

15. The device of claim 14, wherein a first support of the plurality of supports includes a first plurality of anchors and a second support of the plurality of supports includes a second plurality of anchors.

16. The device of claim 14, wherein every support of the plurality of supports includes a separate plurality of anchors.

17. The device of claim 14, wherein each of the plurality of anchors has a tissue engagement end that extends generally toward a proximal end of the expandable frame when the frame is in the collapsed configuration.

18. The device of claim 14, wherein each of the plurality of anchors is integrally formed with one of the plurality of supports.

19. The device of claim 14, wherein the plurality of supports and the plurality of anchors are cut from a tube.

20. The device of claim 14, wherein the plurality of supports are metallic.

21. The device of claim 14, wherein the frame is self-expanding.

22. The device of claim 14, wherein the frame includes a proximal hub and a distal hub.

23. The device of claim 14, further including a barrier attached to a portion of the expandable frame.

24. The device of claim 14, wherein the frame is sized and configured for placement within a left atrial appendage of a patient.

25. An implantable device, comprising:
an expandable frame that is moveable between a collapsed configuration and an expanded configuration, the expandable frame having a proximal end and a distal end;
a plurality of supports, each of the plurality of supports defining a longitudinal axis in the collapsed configuration of the frame and having a length that extends at least partially between the proximal end and the distal end of the frame, each of the plurality of supports including at least one strut and at least one bending region, the at least one bending region having an aspect ratio that is less than an aspect ratio of the at least one strut; and a plurality of anchors attached to a respective one of the plurality of supports, the plurality of anchors including an intermediate anchor, a distal anchor, and a proximal anchor, wherein in the collapsed configuration, the intermediate anchor is positioned at least partially alongside the respective one of the plurality of supports, between the proximal and distal anchors, and spaced laterally from the longitudinal axis of the respective one of the plurality of supports.

26. The device of claim 25, wherein the at least one bending region has an aspect ratio in the range of 1:1 to 2:1.

27. The device of claim 25, wherein the at least one bending region has an aspect ratio in the range of 1.5:1.

28. The device of claim 25, wherein each of the plurality of supports includes at least one jogged portion.

29. The device of claim 25, wherein the plurality of anchors are integrally formed with the respective one of the plurality of supports.

30. The device of claim 25, wherein the plurality of supports and the plurality of anchors are cut from a tube.

31. The device of claim 25, wherein the plurality of supports are metallic.

32. The device of claim 25, wherein the frame is self-expanding.

33. The device of claim 25, wherein the frame includes a proximal hub and a distal hub.

34. The device of claim 25, further including a barrier attached to a portion of the expandable frame.

35. The device of claim 25, wherein the frame is sized and configured for placement within a left atrial appendage of a patient.

36. The device of claim 25, wherein a first support of the plurality of supports includes a first plurality of anchors and a second support of the plurality of supports includes a second plurality of anchors.

37. The device of claim 25, wherein every support of the plurality of supports includes a separate plurality of anchors.

* * * * *